(12) United States Patent
Bayer

(10) Patent No.: US 8,816,046 B2
(45) Date of Patent: Aug. 26, 2014

(54) COMPOSITIONS AND METHODS FOR CAMKII INHIBITORS AND USES THEREOF

(75) Inventor: K. Ulrich Bayer, Denver, CO (US)

(73) Assignee: The University of Colorado, a body corporate, Denver, CO (US)

( * ) Notice: Subject to any disclaimer, the term of this patent is extended or adjusted under 35 U.S.C. 154(b) by 0 days.

(21) Appl. No.: 12/679,459

(22) PCT Filed: Sep. 26, 2008

(86) PCT No.: PCT/US2008/077934
§ 371 (c)(1),
(2), (4) Date: Jul. 9, 2010

(87) PCT Pub. No.: WO2009/042906
PCT Pub. Date: Apr. 2, 2009

(65) Prior Publication Data
US 2010/0285033 A1   Nov. 11, 2010

Related U.S. Application Data

(60) Provisional application No. 60/975,329, filed on Sep. 26, 2007, provisional application No. 60/980,766, filed on Oct. 17, 2007.

(51) Int. Cl.
*A61K 38/10* (2006.01)
*C07K 14/00* (2006.01)

(52) U.S. Cl.
USPC ......................................... 530/326; 514/17.7

(58) Field of Classification Search
None
See application file for complete search history.

(56) References Cited

U.S. PATENT DOCUMENTS

| 2003/0148389 A1 | 8/2003 | Bihain et al. |
| 2003/0236188 A1 | 12/2003 | Spytek et al. |
| 2006/0073472 A1 | 4/2006 | Watterson et al. |
| 2006/0148711 A1 | 7/2006 | Lu et al. |

OTHER PUBLICATIONS

Snyder et al. Cell Penetrating Peptides in Drug Delivery, Mar. 2004, Pharmaceutical Research 21(3):389-393.*
International Search Report and Written Opinion of the International Searching Authority, PCT/US08/77934, Dec. 24, 2008.
Biala et al., "The reinforcing effects of chronic D-amphetamine and morphine are impaired in a line of memory-deficient mice overexpressing calcineurin." Eur J. Neurosci. Jun. 21, 2005(11); 3089-3096.
Aarts, M.M. & Tymianski, M. Molecular mechanisms underlying specificity of excitotoxic signaling in neurons. Curr Mol Med 2004; 4: 137-47.
Bramlett, H.M. & Dietrich, W.D. Pathophysiology of cerebral ischemia and brain trauma: similarities and differences. J Cereb Blood Flow Metab 2004; 24: 133-50.
Chauhan, A., Tikoo, A.m Kapur, A.K., & Singh, M. The taming of the cell penetrating domain of the HIV Tat: Myth and realities. J. Contr. Release 2007; 117: 148-162.
Coultrap, S.J., Vest, R.S., Ashpole, N.M. & Hudmon, A. & Bayer, K.U. CaMKII in cerebral ischemia. Acta Pharm. Sinica 2011; 32: 861-872. 13.
Doyle, K.P., Simon, R.P. & Stenzel-Poore, M.P. Mechanisms of ischemic brain damage. Neuropharmacology 2008; 55: 310-8.
Hara, M.R. & Snyder, S.H. Cell signaling and neuronal death. Annu Rev Pharmacol Toxicol 2007; 47: 117-41.
Mattson, M. Excitotoxic and excitoprotective mechanisms. In NeuroMolecular Medicine vol. 3 65-94 (Humana Press Inc., 2003).
Vest, R.S., O'Leary, H., Coultrap, S.J., Kindy, M.S. & Bayer, K.U. Effective post-insult neuroprotection by a novel Ca(2+)/ calmodulin-dependent protein kinase II (CaMKII) inhibitor. J Biol Chem 2010; 285: 20675-82.

* cited by examiner

*Primary Examiner* — John Ulm
(74) *Attorney, Agent, or Firm* — Faegre Baker Daniels LLP

(57) ABSTRACT

Embodiments herein generally relate to methods, compositions and uses of CaMKII inhibitors. Other embodiments relate to methods, compositions and uses of agents that target CaMKII. Yet further embodiments relate to compositions, methods and uses of CaMKIIN-derived molecules and other CaMKII inhibitor molecules that inhibit autonomous CaMKII activity. In accordance with these embodiments, compositions that inhibit autonomous CaMKII activity may be used for treating conditions causing neuronal cell death, for treating cancer or for treating neurodegenerative disorders.

9 Claims, 24 Drawing Sheets

Figs. 1A-1D
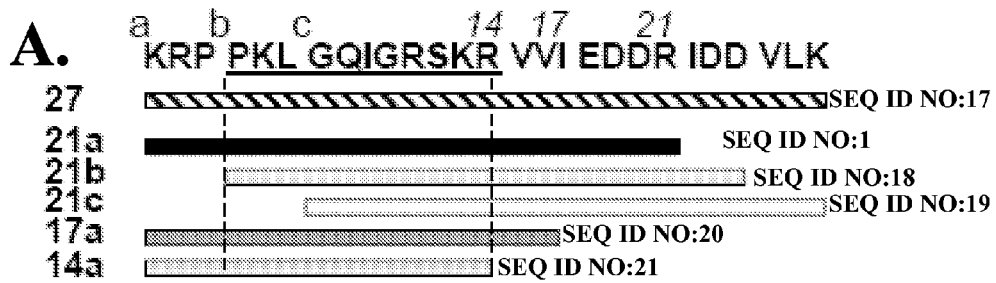
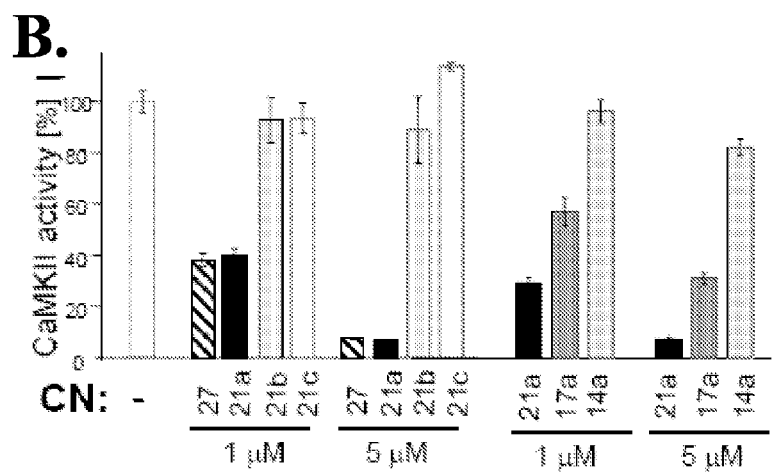
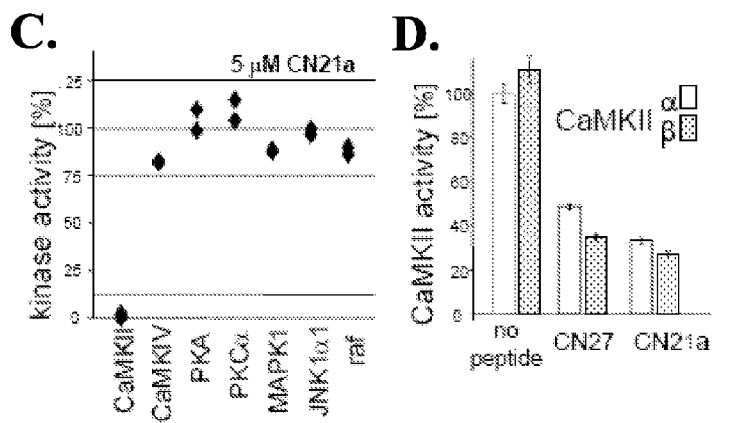

Figs. 9A-9E.
A.
ant: RQIKIWFQNRRMKWK(K)  SEQ ID NO:16
tat: YGRKKRRQRRR  SEQ ID NO:15
CN: KRP PKLGQIGRSKRVVI ED DR IDDVLK  SEQ ID NO:27
              ▲                  ▲19 21        27
B. 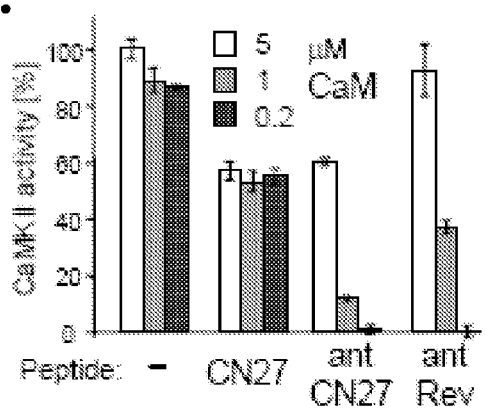
D. 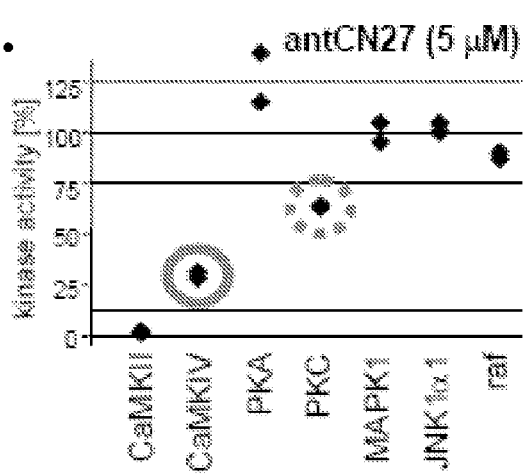
C. 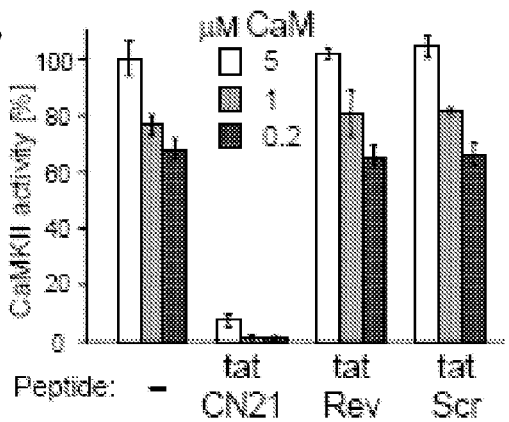
E. 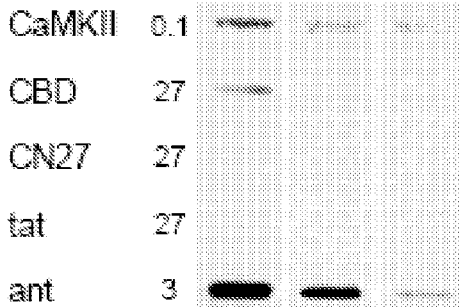

F.

G.

Figs. 12A-12D
A.
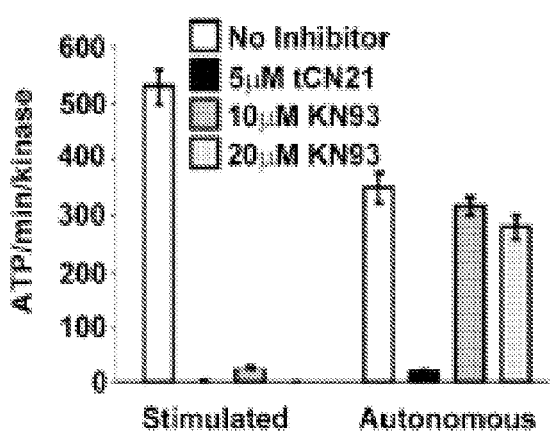
B.
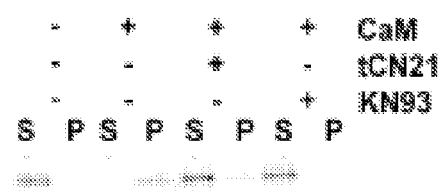
C.
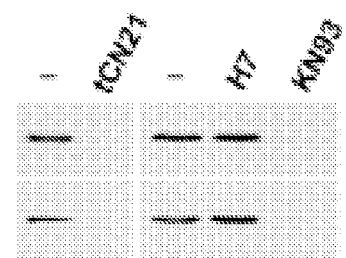
D.
| | tCN21 | KN93 |
|---|---|---|
| Inhibits CaM/Ca2+ Stimulated Activity: | Yes | Yes |
| Inhibits Autonomous Activity: | Yes | No |
| Inhibits NR2B Binding: | Yes | Yes |
| Inhibits Self-Association: | Yes | Yes |

Figs. 18A-18C
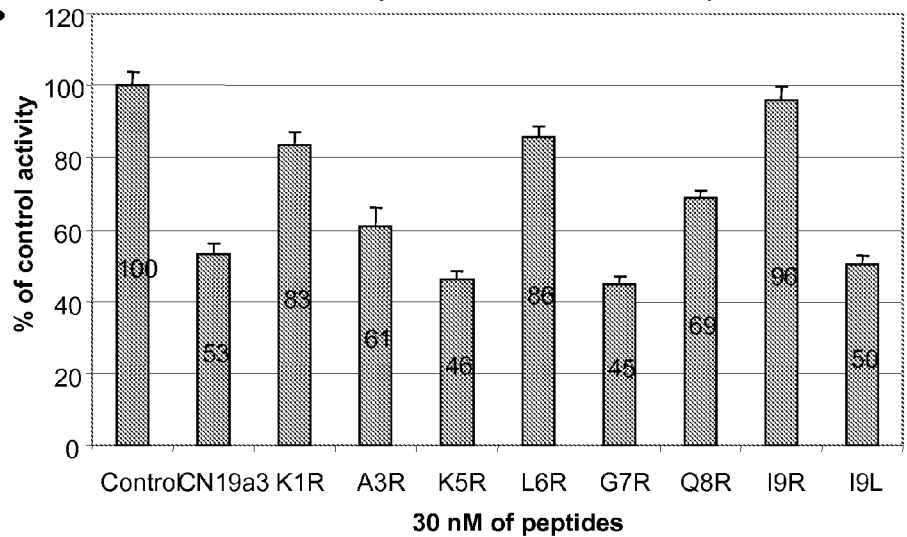
A. Argnine substitutions of CN19-a3 (P3,K13,R14->A mutant)
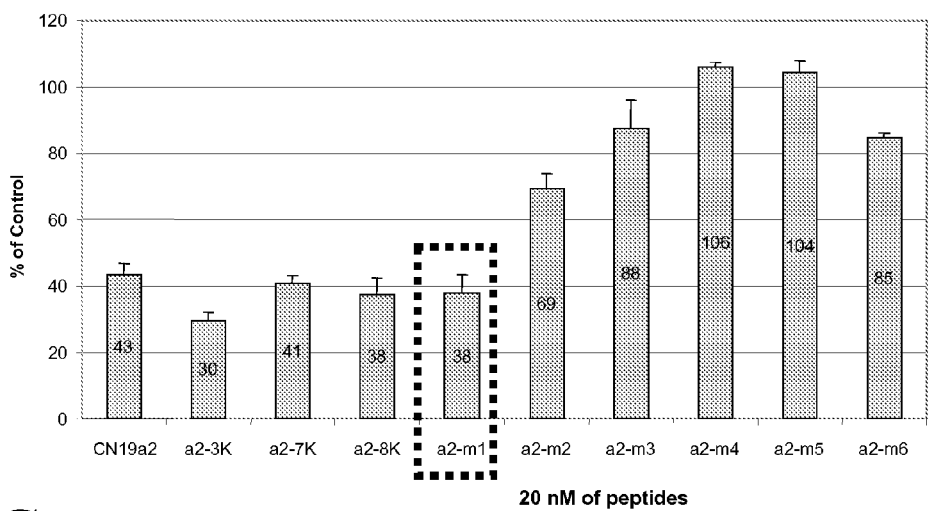
B. Argnine substitution combinations of CN19-a2 (P3,R14->A mutant)
C.
CN19-a2  -m1   3, 5, 7, 12 R
         -m2   3, 5, 7, 12R, 19A
         -m3   5, 7, 12 R, 19A
         -m4   3, 5, 7, 12R, 17R, 19A
         -m5   3, 5, 7, 12R, 17K, 19A
         -m6   3, 5, 7, 12R, 8K, 19A

A.

B.

COMPOSITIONS AND METHODS FOR CAMKII INHIBITORS AND USES THEREOF

RELATED APPLICATIONS

The present PCT application claims the benefit of U.S. Provisional Patent Applications Ser. No. 60/975,329, filed Sep. 26, 2007 and Ser. No. 60/980,766, filed Oct. 17, 2007, incorporated herein by reference in their entirety.

FEDERALLY FUNDED RESEARCH

Some embodiments disclosed herein were supported in part by NIH/NINDS grant numbers (R01) NS052644 and (R03) NS050120 from the National Institutes of Health. The U.S. Government has certain rights to the subject invention.

FIELD

Embodiments herein generally relate to methods, compositions and uses of CaMKII inhibitors. In addition, embodiments herein generally relate to methods, compositions and uses of agents that target CaMKII. Other embodiments relate to compositions, methods and uses of CaMKIIN-derived molecules and other molecules that inhibit autonomous CaMKII activity, of use to treat neurodegenerative disorders, neuronal cell death or subjects after acute insult.

BACKGROUND

CaMKII is a multifunctional protein kinase known for its critical role in learning and memory. CaMKII is highly expressed in the brain, but at least one of its four isoforms ($\alpha$, $\beta$, $\gamma$ and $\delta$) has been found in every cell type examined. Numerous cellular functions of CaMKII have been described, both in and outside the nervous system. Some of these functions include regulation of various ion channels, gene expression, cell cycle/proliferation control, apoptotic and excitotoxic cell death cell morphology and filopodia motility. CaMKII is also implicated in regulation of insulin secretion, although studies suggesting this were largely based on KN inhibitors that also affect Ca2+-channels required for secretion.

CaMKII forms multimeric holoenzymes and a CaM-dependent inter-subunit auto-phosphorylation at T286 renders the kinase active even after dissociation of Ca2+/CaM. T286 is located in the regulatory region; its phosphorylation relieves auto-inhibition by preventing binding of the region around T286 to the T-site, which is adjacent to the substrate binding S-site. The Ca2+-independent or autonomous activity has been regarded as a form of "molecular memory", and is important in several neuronal functions of the kinase. Additionally, T286 phosphorylation traps CaM on CaMKII, and regulates CaMKII binding to other proteins, such as syntaxin, densin-180, NR1, NR2A, NR2B, and F-actin. Among the other auto-phosphorylation sites, functions of T305/306 are understood best. T305/306 auto-phosphorylation can occur in an intra-subunit reaction, blocks CaM binding, accelerates CaMKII dissociation from synaptic sites, and also plays a role in learning.

CaMKII inhibitors such as KN62, KN93, and peptides derived from the auto-inhibitory region of CaMKII, such as AIP or ACS-I, are useful tools for examining functions of the kinase. However, the KN drugs can not discriminate between CaMKII and CaMKIV and they inhibit voltage-gated K+ and Ca2+ channels. Moreover, the KN drugs interfere competitively with activation by CaM and thus do not inhibit autonomous activity of the kinase. The CaMKII-derived peptide inhibitors are widely believed to be more specific. However, such peptides also inhibit other CaM-dependent kinases as well as protein kinase A, and their potency is low. Thus, more specific inhibitor molecules are needed for targeting CaMKII.

SUMMARY

Embodiments of the present invention provide for methods, compositions and uses of CaMKII inhibitor protein CaM-KIIN. Certain embodiments concern compositions including at least a portion of the CaMKII inhibitor protein CaM-KIIN. Some embodiments concern compositions of about 5, to about 10, to about 20, to about 25, to about 30, to about 40, to about 50, to about 100 or more consecutive amino acids of CaM-KIIN. In accordance with these embodiments, CaM-KIIN molecules or fragments thereof can be administered as a composition alone, linked to a transporter agent, associated with microparticles, or other delivery system. In other embodiments, a peptide derived from a CaM-KIIN molecule may include one or more amino acids that differ from native CaM-KIIN. In accordance with these embodiments, amino acid changes within a peptide derived from CaM KIIN may increase, decrease or maintain potency of CaMKII inhibition.

Other embodiments herein can concern a composition of a fragment, portion or truncated form of CaM-KIIN linked to cell penetrating sequences. For example, a 'tat,' or an 'ant' sequence (tat: YGRKKRRQRRR, SEQ ID NO:15; ant: RQIKIWFQNRRMKWK, SEQ ID NO:16), meristyl-group, palmityl-group or combination thereof, can be covalently or non-covalently associated with a portion of CaM-KIIN. Other embodiments herein concern a modified portion of CaM-KIIN made cell penetrating or a modified CaM-KIIN molecule, derivative of or fragment thereof designed to have a longer half-life or increased potency for inhibition of CaMKII. In certain embodiments, the fragment or portion of CaM-KIIN can be 5 consecutive amino acids or more of SEQ ID NO:1. In other embodiments, compositions contemplated herein can include one or more peptides derived from SEQ ID NO:1 including 30 or less amino acids in length, 25 or less amino acids in length, 20 or less amino acids in length, or 15 or less amino acids in length.

Other embodiments concern compositions and methods for reducing neuronal cell death in a subject. In accordance with these embodiments, compositions contemplated herein can be used to treat a subject having or at risk of developing a neurodegenerative disease. In certain embodiments, compositions disclosed herein can be used to decrease progression of neurodegenerative disease or disorders. Disorders can include, but are not limited to, stroke, ischemia, traumatic brain injury, Alzheimer's disease, Parkinson's disease, drug addiction, spinal cord injury, regulation of insulin secretion, or cancer. In other embodiments, compositions and methods contemplated herein can be used to treat a subject having a brain injury for example, a traumatic brain injury. In some embodiments, compositions and methods herein can be used to reduce, inhibit or prevent toxic effects of excessive excitatory neurotransmitters. For example, one exemplary neurotransmitter may be glutamate. In certain embodiments, reduction of toxic effects of excessive excitatory neurotransmitters may be at least a 10%, or at least a 15%, or at least a 25%, or at least a 50%, or more reduction in side effects due to toxic effects of excessive excitatory neurotransmitters. In some particular embodiments, side effects can include, but are not limited to, cell death, neuronal activation and/or neuronal translocation. In certain embodiments, a composition contemplated for reducing neuronal cell capacity can include 5, 10, 20, 25, 30, 40, 50, 100 or more consecutive amino acids of CaM-KIIN protein alone, or linked to or associated with a cell-transporter/penetrating agent.

In other embodiments, CaMKII inhibitor peptides (hereinafter "CN peptides") are optimized by means known in the art. For example, CN peptides can be made to have increased cell-penetrating capabilities, increased potency to inhibit CaMKII and/or increased stability. In certain embodiments, CN peptides can be made cell-penetrating where such cell-penetrating CN peptides can be protective from glutamate excitotoxicity even when applied after an insult occurs to a subject. In other embodiments, autonomous CaMKII activity can be a target for post-insult neuro-protection, for example, administering CaM-KIIN molecules or fragments or other molecules that target autonomous CaMKII activity to a subject in need of such a treatment. In yet other embodiments, mutant forms of the inhibitory region of CaM-KIIN can be derived with increased potency of inhibition and used in compositions and methods disclosed herein. In some embodiments, a composition of a peptide including 25% or more consecutive amino acids of SEQ ID NO:1, CN21, alone or fused to a cell-penetrating agent is contemplated of use herein. In other embodiments, a composition of a peptide including 25% or more consecutive amino acids of SEQ ID NO:2, CN19, alone or fused to a cell-penetrating agent is contemplated of use herein.

It is contemplated that administration to a subject in need thereof of any of the disclosed compositions may be used alone or in combination with other agents used to treat conditions herein (e.g. neuronal cell death, acute insult, traumatic brain injury, stroke, neurodegenerative conditions).

BRIEF DESCRIPTION OF THE DRAWINGS

The following drawings form part of the present specification and are included to further demonstrate certain embodiments herein. The embodiments may be better understood by reference to one or more of these drawings alone or in combination with the detailed description of specific embodiments presented.

FIGS. 1A-1D represent an exemplary amino acid sequences of a portion of CaM-KIIN, SEQ ID NO:1, (FIG. 1A). 1B represents an exemplary histogram of CaMKII activity measured in the presence of indicated portions of CaM-KIIN. 1C represents exemplary kinases tested for inhibition of activity in the presence of various agents. 1D represents exemplary effects of CN27 and CN21 on CaMKII isoforms.

FIGS. 9A-9G illustrate ant and tat fusion to an inhibitor peptide and their direct binding to calmodulin. 9A illustrates that the ant and tat sequences fused to the N-terminus of CNs. 9B represents an exemplary histogram that illustrates extent of CaMKII inhibition by antCN27 and the reverse sequence control antRev depended on the CaM concentration. 9C represents an exemplary histogram illustrating tatCN21 inhibited CaMKII-mediated AC3 phosphorylation at all CaM concentrations, while the reverse and scrambled sequence controls tatRev and tatScr had no effect compared to assays without tat peptide. 9D represents an exemplary plot of kinase activity in the presence of various agents. 9E represents exemplary binding of biotinylated CaM to peptides immobilized by slot blot. 9F represents an exemplary blot overlay assay in the presence or absence of various peptides. 9G represents an exemplary plot of fluorescence of TA-CaM in the presence or absence of antCN27, ant or tatCN21.

FIGS. 12A-12D represents exemplary data of KN93 and tatCN21 effects on CaMKII. 12A represents an exemplary histogram of tatCN21 and KN93 effects on calcium and calmodulin stimulated CaMKII activity. 12B represents an exemplary blot representing self-association in vitro in the presence or absence of KN93 or tatCN21. 12C represents an exemplary Western analysis measuring binding to the immobilized NR2B subunit of the NMDAR in the presences or absence of tatCN21, KN93, or a non-specific kinase inhibitor, H7. TatCN21 and KN93. 12D represents an exemplary table summarizing effects of tatCN21 and KN93 on CaMKII activity, NR2B binding, or self-association.

FIGS. 18A-18C represent exemplary data of several point mutations to an Arginine (R) and their effect on potency of CaMKII inhibition. 18A represents an exemplary histogram of percent of control in the presence of various mutations of CN19-a3. 18B represents an exemplary histogram of a mutant, CN19a2-m1 and its effects on inhibitory potency. 18C illustrates additional mutations made in the combination mutant series.

DEFINITIONS

Figure 2A:
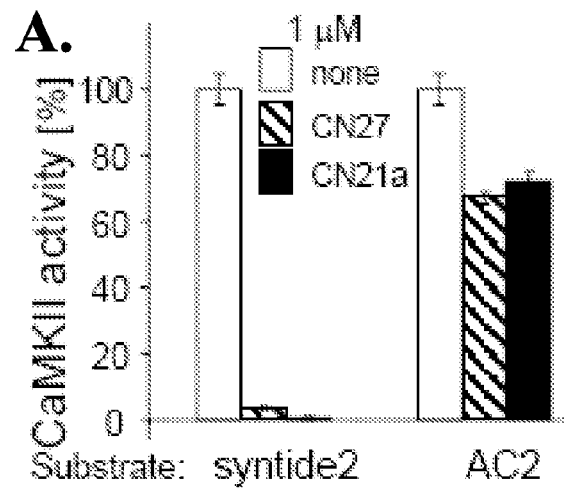
FIGS. 2A-2C represent exemplary effects of CN peptides on phosphorylation of two peptide substrates. 2A represents effects of CN peptides on phosphorylation of peptide substrate syntide2. 2C represents a competition assay between CN21 and AC2.

As used herein, "a" or "an" may mean one or more than one of an item.

As used herein, vessel can include, but is not limited to, test tube, mini- or micro-fuge tube, channel, vial, microliter plate or container.

As used herein the specification, "subject" or "subjects" may include but are not limited mammals such as humans or mammals, domesticated or wild, for example dogs, cats, ferrets, rabbits, pigs, horses, cattle, zoo animals, or wild animals.

As used herein, "about" can mean plus or minus ten percent.

An "antibody" as used herein refers to a full-length (i.e., naturally occurring or formed by normal immunoglobulin gene fragment recombinatorial processes) immunoglobulin molecule (e.g., an IgG antibody) or an immunologically active (i.e., specifically binding) portion of an immunoglobulin molecule, like an antibody fragment. The term "antibody" also includes "humanized" antibodies and even fully human antibodies that can be produced by phage display, gene and chromosome transfection methods, as well as by other means. This term also includes monoclonal antibodies, polyclonal antibodies, multivalent antibodies, multispecific antibodies (e.g., bispecific antibodies).

"Polyclonal antibodies" are generated in an immunogenic response to a protein having many epitopes. A composition (e.g., serum) of polyclonal antibodies thus includes a variety of different antibodies directed to the same and to different epitopes within the protein. Methods for producing polyclonal antibodies are known in the art (see, e.g., Cooper et al., Section III of Chapter 11 in: *Short Protocols in Molecular Biology*, 2nd Ed., Ausubel et al., eds., John Wiley and Sons, New York, 1992, pages 11-37 to 11-41).

A "monoclonal antibody" is a specific antibody that recognizes a single specific epitope of an immunogenic protein. In a plurality of a monoclonal antibody, each antibody molecule is identical to the others in the plurality. In order to isolate a monoclonal antibody, a clonal cell line that expresses, displays and/or secretes a particular monoclonal antibody is first identified; this clonal cell line can be used in one method of producing the antibodies of the present invention. Methods for the preparation of clonal cell lines and of monoclonal antibodies expressed thereby are known in the art (see, for example, Fuller et al., Section II of Chapter 11 in: *Short Protocols in Molecular Biology*, 2nd Ed., Ausubel et al., eds., John Wiley and Sons, New York, 1992, pages 11-22 to 11-11-36).

DETAILED DESCRIPTION

In the following sections, various exemplary compositions and methods are described in order to detail various embodiments of the invention. It will be obvious to one skilled in the art that practicing the various embodiments does not require the employment of all or even some of the specific details outlined herein, but rather that sequences chosen, proteins selected, samples, concentrations, times and other specific details may be modified through routine experimentation. In some cases, well-known methods or components have not been included in the description.

CaMKII is a multifunctional protein kinase best known for its critical role in learning and memory. CaMKII is highly expressed in the brain, but at least one of its four isoforms ($\alpha$, $\beta$, $\gamma$ and $\delta$) has been found in every cell type examined. Numerous cellular functions of CaMKII have been described, both in and outside the nervous system. These include regulation of various ion channels, gene expression, cell cycle/proliferation control, apoptotic and excitotoxic cell death, cell morphology and filopodia motility. CaMKII has also been implicated in regulation of insulin secretion, however, this conclusion is largely based on experiments using KN inhibitors, which also affect the Ca2+-channels required for secretion (see below).

CaMKII forms multimeric holoenzymes and a CaM-dependent inter-subunit auto-phosphorylation at T286 renders the kinase active even after dissociation of Ca2+/CaM. Phosphorylation of T286, which is located in the regulatory region, relieves auto-inhibition by preventing binding of the region around T286 to the T-site, which is adjacent to the substrate binding S-site (see kinase domain model in FIG. 3A). The subsequent Ca2+-independent or autonomous activity has been regarded as a form of "molecular memory", and it is important in several neuronal functions of the kinase. Additionally, T286 phosphorylation traps CaM on CaMKII, and regulates CaMKII binding to other proteins, such as syntaxin, densin-180, NR1, NR2A, NR2B, and F-actin. Other auto-phosphorylation sites previously examined are functional consequences of T305/306 phosphorylation. T305/306 auto-phosphorylation can occur in an intra-subunit reaction, blocks CaM binding, accelerates CaMKII dissociation from synaptic site, and also plays a role in learning.

CaMKII inhibitors such as KN62, KN93, and peptides derived from the autoinibitory region of CaMKII, such as AIP or AC3-I, are useful tools for examining functions of the kinase. However, the KN drugs can not discriminate between CaMKII and CaMKIV and they inhibit voltage-gated K+ and Ca2+ channels. Moreover, the KN drugs interfere competitively with activation by CaM and thus do not inhibit autonomous activity of the kinase. The CaMKII-derived peptide inhibitors are widely believed to be more specific. However, such peptides also inhibit other CaM-dependent kinases as well as protein kinase A, and their potency is low. Thus, embodiments herein concern a natural CaMKII inhibitor protein, CaM-KIIN because it may provide a promising alternative to other inhibitors, as it potently inhibits only CaMKII.

Some embodiments concern compositions that can include a region of CaM-KIINα that retains full potency and specificity of CaMKII inhibition (referred to as CN21) (the homologous CaM-KIINβ region differs at one residue only). In accordance with these embodiments, CN21 efficiently blocked substrate- and T305 auto-phosphorylation of CaMKII, but only mildly affected T286 auto-phosphorylation. Identification of the T-site as the CaM-KIIN interaction site on CaMKII provided two mechanisms for this novel differential inhibitor effect: CaM-KIIN was competitive with the region around T286, and strengthened the CaM binding required for presentation of T286 as a substrate. In other embodiments, compositions, for example, peptides comprising a portion of the CaM-KIIN molecule can be fused to a transporter agent. In certain embodiments, Tat-fused CN21 can be generated to increase cell penetrating capabilities. In addition, compositions disclosed herein may be used for studying cellular CaMKII function.

In certain embodiments, compositions and methods including a natural CaMKII inhibitor protein CaM-KIIN can be used to inhibit CaMKII with little or no effect on CaMKI, CaMKIV, PKA or PKC. In other embodiments, two forms of CaM-KIIN are contemplated (e.g. isoforms). These isoforms are highly homologous to each other and co-localize with microtubules in neurons; both bind selectively to CaMKII only in its activated states. In more particular embodiments, compositions, methods and uses for short CaM-KIIN-derived peptides are contemplated herein.

In certain embodiments, inhibitors of CaMKII are generated from various regions of CaMKIIN inhibitory region. In one embodiment, minimal inhibitory CN regions are identified. In accordance with these embodiments, kinase assays can be performed in order to assess certain inhibition of CaMK molecules such as CaMKII or CaMKI. In one example, a molecule referred to herein as CN19 is identified as a minimal inhibitory region of CaM-KIIN having near-maximal potency (CN19, SEQ ID NO:2). Further truncations led to significant reduction in potency of inhibition of CaMKII activity towards peptide substrates. (Note, a shorter core sequence is still able to significantly reduce phosphorylation of protein substrates). In certain embodiments, potency of CaMKII inhibition by CN19 can be modulated by mutations. One of a more notable increase of potency was by the R14A mutations, which increased potency over 10 fold, bringing the IC50 into the low nM range. Also notable, S12 can be mutated without detriment or even with slight benefit to potency (only by very specific substitution, V and R, but not by others); this can prevent phosphorylation of S12 and thereby prevent inactivation (see FIG. 22B).

In certain embodiments, fusion of truncated forms or portions of CaMKIIN to cell penetrating agents can be performed. Cell penetrating agents contemplated herein can include, but is not limited to, tat, ant, meristyl-groups, palmityl-groups, and other related or derived peptide and lipid compounds, as well as mimicking non-peptide and non-lipid compounds. In certain examples, tat can be fused or covalently or non-covalently attached to CN peptides, for example fused to CN21, CN19, CN17 or CN27 or mutant or variant thereof. Different forms of fusion can be performed in order to design certain molecules. For example, fusions may be at the C-terminus instead of the N-terminus, use different cell penetration-mediating compound; addition or reduction of linker sequences; use of overlapping sequences; fusion by other covalent or non-covalent means, including by disulfide bonds between added cysteines, which would be cleaved within cells.

In some embodiments, CN19, was shown to be the maximal truncation not resulting in significant reduction of inhibitory potency even though further truncations still show significant inhibition of CaMKII activity. In other embodiments, a 14 mer was still effective for inhibition of protein but not peptide phosphorylation by CaMKII. In addition, CN19 also retained specificity (e.g. it did not significantly affect the closely related protein kinase CaMKI).

Other embodiments herein relate to obtaining portions of CaM-KIIN and mutating or substituting one or more amino acids in the portions to alter potency of the portions for inhibiting CaMKII activity. In certain embodiments, mutations are generated to increase CaMKII inhibition. For example, mutational analysis of CN19 demonstrated that inhibitory potency can be significantly further enhanced. In one example, an Alanine (Ala) scan (individual amino acid substitutions with Ala) identified 3 amino acid positions (P3, K13, R14) for which Ala mutants had a clearly enhanced inhibitory potency; several additional amino acid positions had slightly enhanced potency or no effect. Additionally, amino acid positions can be replaced with positive residues (R or K) without loss of inhibitory potency. For example, this could be used to further enhance cell-penetration. In other embodiments, it is contemplated that molecules of CaM-KIIN portions can be altered to reduce phosphorylation of the portions which can alter potency of inhibition. For example, CN19 contains one amino acid, Ser12, that could be phosphorylated (e.g. by PKC) within cells, thereby reducing CN19's inhibitory effect. In one example, a single mutant R14A was very potent. S12 can be mutated, for example to R or V, without loss of potency. In certain methods disclosed herein, it may be desirable to have a composition having increased inhibitory potency compared to a wild type CN molecule composition. For example, an increase in potency for R14A was found to be greater than 10 fold, bringing the IC50 into the single digit nM range.

In certain embodiments, CN inhibitors contemplated herein can be made to be cell-penetrating. In other embodiments, compositions contemplated herein may be administered to a cell or to a subject by any method known in the art (e.g. microbeads, microspheres, microparticles, slow release gel). In other embodiments, CN inhibitors can be made efficiently cell-penetrating by for example, covalent fusion with the cell-penetrating ant (derived from the antennapedia protein; also called penetratin, SEQ ID NO:16) or tat (from the HIV tat protein, SEQ ID NO:15) sequences. However, in certain exemplary methods ant was found to interfere with general calmodulin signaling (thereby interfering with specificity) by direct binding to calmodulin, and effect further enhanced by ant fusion to CN27 (SEQ ID NO:17). By contrast, tat or tatCN21 did not bind to calmodulin, making tatCN peptides viable cell penetrating inhibitors.

Other alternative methods may be used to make CN peptides cell penetrating including, but not limited to, fusion with other cell penetrating peptide sequences (e.g. various modifications of the tat sequence) or lipophilic compounds (such as myristyl groups). These fusions can be either at the N-terminus or at the C-terminus, with or without additional linkers or with removal of partially overlapping or exchangeable sequences. Any such fusions can also be made through disulfide bonds, allowing cleavage of the CN compound and the cell-penetration mediating compound in the reducing environment within cells, or other non-covalent or covalent bonds.

In certain embodiments, cell-penetrating CN inhibitors can protect from glutamate excitotoxicity. In other embodiments, cell-penetrating CN inhibitors can protect from glutamate excitotoxicity after insult. tatCN21 showed a significant neuro-protective effect during glutamate excitotoxicity, a cell culture model of stroke and other neurological conditions. Importantly, neuro-protection was observed even when the compound was applied significantly after the insult, thus opening a clinically relevant window of therapeutic opportunity. In one example, tatCN21 showed significant neuroprotection both when present during insult or when added after insult. Some embodiments concern identification of a drug target for post-insult neuro-protection. Knowledge of the actual drug targets will allow a relatively easy high-throughput screening for additional and/or alternative therapeutic compounds. It is contemplated herein that CaMKII can be targeted using molecules and constructs disclosed and that new constructs and molecules of interest can be identified that selectively inhibit CaMK molecules, for example CaMKII.

Neuronal Cell Death

In certain embodiments, glutamate excitotoxicity is contemplated to be a cause of neuronal cell death in acute conditions. Conditions include, but are not limited to stroke, global ischemia (e.g. caused by suffocation or cardiac arrest), or traumatic brain injury (e.g. caused by accidents, assaults, and explosions). Additionally, glutamate is considered to be involved in chronic neurodegenerative diseases. Chronic neurodegenerative diseases include, but are not limited to Alzheimer's and Parkinson's. It is contemplated that compositions disclosed herein can be of use to reduce, prevent or treat conditions that cause neuronal death in a subject in need thereof. In other embodiments, compositions and methods disclosed herein may be of use as novel inhibitors for subjects having an addiction or undergoing cancer treatment. For example, CaMKII has been demonstrated to be involved in addiction, and CaMKII inhibitors have been shown to promote death of cancer cells (and to enhance the effect of other cancer-cell treating drugs). Therefore, it is contemplated herein that compositions and methods herein may be used to treat a subject having cancer. In certain embodiments, compositions and methods disclosed herein may be combined with other anti-cancer treatments (e.g. radiation, chemotherapy, hyperthermia) for treating a subject having cancer. In accordance with these embodiments, it is contemplated that CN21 and/or CN19 conserved, or with one or more mutation or addition, may be of use to treat a subject having cancer. In certain embodiments, compositions and methods disclosed herein may be of use to promote cancer cell death in a subject.

Some embodiments herein concern administering a therapeutically effective amount of a composition disclosed herein to a subject having a neurodegenerative disorder. In certain embodiments, compositions disclosed herein may be of use to reduce, prevent inhibit and/or treat conditions leading to neuronal death in a subject in need thereof. In other embodiments, compositions and methods disclosed herein may be combined with any treatment for neurodegenerative disorders or conditions causing neuronal cell death known in the art.

Nucleic Acids

As described herein, an aspect of the present disclosure concerns isolated nucleic acids and methods of use of isolated nucleic acids. The term "nucleic acid" is intended to include DNA and RNA and can be either be double-stranded or single-stranded. In a preferred embodiment, the nucleic acid is a cDNA comprising a nucleotide sequence such as found in GenBank. In certain embodiments, the nucleic acid sequences disclosed herein have utility as hybridization probes or amplification primers. These nucleic acids may be used, for example, in diagnostic evaluation of tissue samples. In certain embodiments, these probes and primers consist of oligonucleotide fragments. Such fragments should be of sufficient length to provide specific hybridization to a RNA or DNA tissue sample. The sequences typically will be 10-20 nucleotides, but may be longer. Longer sequences greater than 50 even up to full length, are preferred for certain embodiments.

In certain embodiments, it will be advantageous to employ nucleic acid sequences in combination with an appropriate means, such as a label, for determining hybridization. A wide variety of appropriate indicator means are available (i.e. fluorescent, radioactive, enzymatic or other ligands, such as avidin/biotin) that are capable of being detected. In preferred embodiments, one may desire to employ a fluorescent label or an enzyme tag such as urease, alkaline phosphatase or peroxidase, instead of radioactive or other environmentally undesirable reagents. In the case of enzyme tags, colorimetric indicator substrates are known which can be employed to provide a detection means visible to the human eye or spectrophotometrically, to identify specific hybridization with complementary nucleic acid-containing samples.

In general, it is envisioned that the hybridization probes described herein will not only be useful in solutions as in PCR, for detection of expression of corresponding genes but also in embodiments employing a solid phase. In embodiments involving a solid phase, the test DNA (or RNA) is adsorbed or otherwise affixed to a selected matrix or surface. This fixed, single-stranded nucleic acid is then subjected to hybridization with selected probes under known conditions.

The gene or gene fragment encoding a polypeptide (e.g. CaM-KIIN or portion thereof) may be inserted into an expression vector by standard subcloning techniques. An *E. coli* expression vector may be used which produces the recombinant polypeptide as a fusion protein, allowing rapid affinity purification of the protein. Examples of such fusion protein expression systems are the FLAG system (IBI, New Haven, Conn.), and the 6.times.His system (Qiagen, Chatsworth, Calif.).

Any expression vector (e.g. mammalian, yeast, bacterial etc) known in the art is contemplated for expression of CaM-KIIN constructs or derivatives, or other CaMKII inhibitor molecule constructs etc.

A recombinant expression vector may be a plasmid. The recombinant expression vector further may be a virus, or portion thereof, which allows for expression of a nucleic acid introduced into the viral nucleic acid.

Recombinant expression vectors can be designed for expression of peptides or peptide constructs contemplated herein. For example, proteins can be expressed in bacterial cells such as *E. coli*, insect cells (using baculovirus), yeast cells or mammalian cells.

One embodiment includes isolated nucleic acids encoding proteins having biological activity of CaMKII inhibition. The term "isolated" refers to a nucleic acid substantially free of cellular material or culture medium when produced by recombinant DNA techniques, or chemical precursors or other chemicals when chemically synthesized. An "isolated" nucleic acid is also free of sequences that naturally flank the nucleic acid (i.e., sequences located at the 5' and 3' ends of the nucleic acid) in the organism from which the nucleic acid is derived.

It will be appreciated that isolated nucleic acids includes nucleic acids having substantial sequence homology with the nucleotide sequence of portions of CaM-KIIN that have CaMKII inhibitory activity.

Proteins comprising an amino acid sequence that is 50%, 60%, 70%, 80% or 90% homologous with the amino acid of CaM-KIIN may provide proteins having CaMKII inhibitory activity.

A nucleic acid of the embodiments, for instance an oligonucleotide, can also be chemically synthesized using standard techniques. Various methods of chemically synthesizing polydeoxynucleotides are known, including solid-phase synthesis which, like peptide synthesis, has been fully automated in commercially available DNA synthesizers (See i.e., Itakura et al. U.S. Pat. No. 4,598,049; Caruthers et al. U.S. Pat. No. 4,458,066; and Itakura U.S. Pat. Nos. 4,401,796 and 4,373,071).

Protein Purification

Various methods for quantifying the degree of purification of the protein or peptide will be known to those of skill in the art in light of the present disclosure. These include, for example, determining the specific activity of an active fraction, or analysis by SDS/PAGE to identify the number of polypeptides in a given fraction. A preferred method for assessing the purity of a fraction is to calculate the specific activity of the fraction, to compare it to the specific activity of the initial extract, and to thus calculate the degree of purity, herein assessed by a "-fold purification number". The actual units used to represent the amount of activity will be dependent upon the particular assay technique chosen to follow the purification and whether or not the expressed protein or peptide exhibits a detectable activity.

Methods for purifying various forms of proteins are known. (i.e., Protein Purification, ed. Scopes, Springer-Verlag, New York, N.Y., 1987; Methods in Molecular Biology: Protein Purification Protocols, Vol. 59, ed. Doonan, Humana Press, Totowa, N.J., 1996). The methods disclosed in the cited references are exemplary only and any variation known in the art may be used. Where a protein is to be purified, various techniques may be combined, including but not limited to cell fractionation, column chromatography (e.g., size exclusion, ion exchange, reverse phase, affinity, etc.), Fast Performance Liquid Chromatography (FPLC), High Performance Liquid Chromatography (HPLC), gel electrophoresis, precipitation with salts, pH, organic solvents or antibodies, ultrafiltration and/or ultracentrifugation.

There is no general requirement that the protein or peptide always be provided in the most purified state. Indeed, it is contemplated that less substantially purified products will have utility in certain embodiments. Partial purification may be accomplished by using fewer purification steps in combination, or by utilizing different forms of the same general purification scheme. Methods exhibiting a lower degree of relative purification may have advantages in total recovery of protein product, or in maintaining the activity of an expressed protein.

One embodiment provides isolated proteins having biological activity of CaMKII inhibition. In a certain embodiments, a protein having biological activity of CaMKII inhibition comprises an amino acid sequence found in CaM-KIIN. In other embodiments, a protein having biological activity of CaMKII inhibition comprises an amino acid sequence, aptamer, antibody or antibody fragment or small molecule that is capable of reducing or eliminating CaMKII activity. Other proteins having biological activity of CaMKII inhibition may have substantial sequence homology to the amino acid sequence of CaM-KIIN, and are also encompassed herein. Contemplated herein are use of these proteins, aptamers, antibody, antibody fragment and/or small molecules with CAMKII inhibitor activity to treat a subject including, but not limited to, a subject experiencing neuronal cell death, having had an acute insult (e.g. stroke, global cerebral ischemia, traumatic brain injury), having a drug addiction, having cancer, or having a neurodegenerative disorder.

In certain embodiments, compositions disclosed herein, for example, compositions having a peptide can include a derivative of the peptide wherein one or more amino acids can be substituted with one or more arginine, alanine, valine, lysine or combination thereof or other amino acid substitutions or mutations thereof (e.g. wherein the amino acid sequence is 19 or more consecutive amino acids of SEQ ID NO:1, 2 or 17).

Molecules which bind to a protein including the antibodies, bispecific antibodies and tetrameric antibody complexes, can be used in a method for identifying CaMKII inhibitory molecules by labeling a molecule with a detectable substance, contacting the molecule with cells and detecting the detectable substance bound to the cells.

Another method for the preparation of the polypeptides may use peptide mimetics. Mimetics are peptide-containing molecules that mimic elements of protein secondary structure. The underlying rationale behind the use of peptide mimetics is that the peptide backbone of proteins exists chiefly to orient amino acid side chains in such a way as to facilitate molecular interactions, such as those of antibody and antigen. A peptide mimetic is expected to permit molecular interactions similar to the natural molecule (e.g. CaMKII inhibitory activity). An embodiment includes the use of protein mimetics to mimic the CaMKII inhibitory activity of constructs and molecules disclosed herein.

Carriers (Lipids, Liposomes, Micelles, Polymers, and Nanoparticles)

Any methods for formation of liposomes and micelles may be use and are known in the art. Nanoparticles or nanocapsules formed from polymers, silica, or metals, which are contemplated herein for drug delivery or imaging, have been described. It is contemplated that delivery of constructs disclosed herein may carried out using the above referenced carriers or any carrier known in the art.

Imaging Agents and Radioisotopes

In certain embodiments, molecules, for example, peptides or proteins may be attached to imaging agents of use for imaging and diagnosis of various diseased organs, tissues or cell types. Many appropriate imaging agents are known in the art, as are methods for their attachment to proteins or peptides. Certain attachment methods can involve the use of a metal chelate complex employing, for example, an organic chelating agent such a DTPA attached to the protein or peptide. Target molecules also may be reacted with an enzyme in the presence of a coupling agent such as glutaraldehyde or periodate. Conjugates with fluorescein markers are prepared in the presence of these coupling agents or by reaction with an isothiocyanate.

Non-limiting examples of paramagnetic ions of potential use as imaging agents include chromium (III), manganese (II), iron (III), iron (II), cobalt (II), nickel (II), copper (II), neodymium (III), samarium (III), ytterbium (III), gadolinium (III), vanadium (II), terbium (III), dysprosium (III), holmium (III) and erbium (III), with gadolinium being particularly preferred. Ions useful in other contexts, such as X-ray imaging, include but are not limited to lanthanum (III), gold (III), lead (II), and especially bismuth (III).

Radioisotopes of potential use as imaging or therapeutic agents include astatine$^{211}$, $^{14}$carbon, $^{51}$chromium, $^{36}$chlorine, $^{57}$cobalt, $^{58}$cobalt, copper$^{62}$, copper$^{64}$, copper$^{67}$, $^{152}$Eu, fluorine$^{18}$, gallium$^{67}$, gallium$^{68}$, $^{3}$hydrogen, iodine$^{123}$, iodine$^{124}$, iodine$^{125}$, iodine$^{131}$, indium$^{111}$, $^{52}$iron, $^{59}$iron, $^{32}$phosphorus, $^{33}$phosphorus, rhenium$^{186}$, rhenium$^{188}$, Sc$^{47}$, $^{75}$selenium, silver$^{111}$, $^{35}$sulphur, technicium$^{94m}$ technicium$^{99m}$ yttrium$^{86}$ and yttrium$^{90}$. $^{125}$I is often being preferred for use in certain embodiments, and technicium$^{99m}$ and indium$^{111}$ are also often preferred due to their low energy and suitability for long range detection.

Radioactively labeled proteins or peptides may be produced according to well-known methods in the art. For instance, they can be iodinated by contact with sodium or potassium iodide and a chemical oxidizing agent such as sodium hypochlorite, or an enzymatic oxidizing agent, such as lactoperoxidase. Proteins or peptides may be labeled with technetium-$^{99m}$ by ligand exchange process, for example, by reducing pertechnate with stannous solution, chelating the reduced technetium onto a Sephadex column and applying the peptide to this column or by direct labeling techniques, e.g., by incubating pertechnate, a reducing agent such as SNCl$_2$, a buffer solution such as sodium-potassium phthalate solution, and the peptide. Intermediary functional groups which are often used to bind radioisotopes which exist as metallic ions to peptides include diethylenetriaminepentaacetic acid (DTPA), DOTA, NOTA, porphyrin chelators and ethylene diaminetetracetic acid (EDTA). Also contemplated for use are fluorescent labels, including rhodamine, fluorescein isothiocyanate and renographin.

In certain embodiments, the claimed peptides or constructs may be linked to a secondary binding ligand or to an enzyme (an enzyme tag) that will generate a colored product upon contact with a chromogenic substrate. Examples of suitable enzymes include urease, alkaline phosphatase, (horseradish) hydrogen peroxidase and glucose oxidase. Preferred secondary binding ligands are biotin and avidin or streptavidin compounds. The use of such labels is well known to those of skill in the art. These fluorescent labels are preferred for in vitro uses, but may also be of utility in vivo applications, particularly endoscopic or intravascular detection procedures.

In alternative embodiments, molecules herein may be tagged with a fluorescent marker. Non-limiting examples of photodetectable labels include Alexa 350, Alexa 430, AMCA, aminoacridine, BODIPY 630/650, BODIPY 650/665, BODIPY-FL, BODIPY-R6G, BODIPY-TMR, BODIPY-TRX, 5-carboxy-4',5'-dichloro-2',7'-dimethoxy fluorescein, 5-carboxy-2',4',5',7'-tetrachlorofluorescein, 5-carboxyfluorescein, 5-carboxyrhodamine, 6-carboxyrhodamine, 6-carboxytetramethyl amino, Cascade Blue, Cy2, Cy3, Cy5,6-FAM, dansyl chloride, Fluorescein, HEX, 6-JOE, NBD (7-nitrobenz-2-oxa-1,3-diazole), Oregon Green 488, Oregon Green 500, Oregon Green 514, Pacific Blue, phthalic acid, terephthalic acid, isophthalic acid, cresyl fast violet, cresyl blue violet, brilliant cresyl blue, para-aminobenzoic acid, erythrosine, phthalocyanines, azomethines, cyanines, xanthines, succinylfluoresceins, rare earth metal cryptates, europium trisbipyridine diamine, a europium cryptate or chelate, diamine, dicyanins, La Jolla blue dye, allopycocyanin, allococyanin B, phycocyanin C, phycocyanin R, thiamine, phycoerythrocyanin, phycoerythrin R, REG, Rhodamine Green, rhodamine isothiocyanate, Rhodamine Red, ROX, TAMRA, TET, TRIT (tetramethyl rhodamine isothiol), Tetramethylrhodamine, and Texas Red. These and other luminescent labels may be obtained from commercial sources such as Molecular Probes (Eugene, Oreg.).

Chemiluminescent labeling compounds of use may include luminol, isoluminol, an aromatic acridinium ester, an imidazole, an acridinium salt and an oxalate ester, or a bioluminescent compound such as luciferin, luciferase and aequorin. Diagnostic immunoconjugates may be used, for example, in intraoperative, endoscopic, or intravascular tumor or disease diagnosis.

In various embodiments, labels of use may comprise metal nanoparticles. Methods of preparing nanoparticles are known. Nanoparticles may also be obtained from commercial sources (e.g., Nanoprobes Inc., Yaphank, N.Y.). Modified nanoparticles are available commercially, such as Nanogold® nanoparticles from Nanoprobes, Inc. (Yaphank, N.Y.). Functionalized nanoparticles of use for conjugation to proteins or peptides may be commercially obtained.

Site-Specific Mutagenesis

Site-specific mutagenesis is a technique useful in the preparation of individual peptides, or biologically functional equivalent proteins or peptides, through specific mutagenesis of the underlying DNA. The technique further provides a ready ability to prepare and test sequence variants, incorporating one or more of the foregoing considerations, by introducing one or more nucleotide sequence changes into the DNA. Site-specific mutagenesis allows the production of mutants through the use of specific oligonucleotide sequences which encode the DNA sequence of the desired mutation, as well as a sufficient number of adjacent nucleotides, to provide a primer sequence of sufficient size and sequence complexity to form a stable duplex on both sides of the deletion junction being traversed. Typically, a primer of about 17 to 25 nucleotides in length is preferred, with about 5 to 10 residues on both sides of the junction of the sequence being altered.

In general, the technique of site-specific mutagenesis is well known in the art. As will be appreciated, the technique typically employs a bacteriophage vector that exists in both a single stranded and double stranded form. Typical vectors useful in site-directed mutagenesis include vectors such as the M13 phage. These phage vectors are commercially available and their use is generally well known to those skilled in the art. Double stranded plasmids are also routinely employed in site directed mutagenesis, which eliminates the step of transferring the gene of interest from a phage to a plasmid.

In general, site-directed mutagenesis is performed by first obtaining a single-stranded vector, or melting of two strands of a double stranded vector which includes within its sequence a DNA sequence encoding the desired protein. An oligonucleotide primer bearing the desired mutated sequence is synthetically prepared. This primer is then annealed with the single-stranded DNA preparation, and subjected to DNA polymerizing enzymes such as E. coli polymerase I Klenow fragment, in order to complete the synthesis of the mutation-bearing strand. Thus, a heteroduplex is formed wherein one strand encodes the original non-mutated sequence and the second strand bears the desired mutation. This heteroduplex vector is then used to transform appropriate cells, such as E. coli cells, and clones are selected that include recombinant vectors bearing the mutated sequence arrangement.

The preparation of sequence variants of the selected gene using site-directed mutagenesis is provided as a means of producing potentially useful species and is not meant to be limiting, as there are other ways in which sequence variants of genes may be obtained. For example, recombinant vectors encoding the desired gene may be treated with mutagenic agents, such as hydroxylamine, to obtain sequence variants. Any technique known in the art for generating one or more amino acid changes or mutations in constructs disclosed herein is contemplated (e.g. CaM-KIIN derived constructs).

Pharmaceutical Compositions and Routes of Administration

Aqueous compositions contemplated herein may include an effective amount of a therapeutic peptide, peptide construct, epitopic core region, stimulator, inhibitor, and the like, dissolved or dispersed in a pharmaceutically acceptable carrier or aqueous medium. Aqueous compositions of gene therapy vectors expressing any of the foregoing are also contemplated. The phrases "pharmaceutically or pharmacologically acceptable" refer to molecular entities and compositions that do not produce an adverse, allergic or other untoward reaction when administered to an animal, or a human, as appropriate.

Aqueous compositions contemplated herein may include an effective amount of the compound, dissolved or dispersed in a pharmaceutically acceptable carrier or aqueous medium. Such compositions can also be referred to as inocula. As used herein, "pharmaceutically acceptable carrier" includes any and all solvents, dispersion media, coatings, antibacterial and antifungal agents, isotonic and absorption delaying agents and the like. The use of such media and agents for pharmaceutical active substances is well known in the art. Except insofar as any conventional media or agent is incompatible with the active ingredient, its use in the therapeutic compositions is contemplated. Supplementary active ingredients can also be incorporated into the compositions. For human administration, preparations should meet sterility, pyrogenicity, general safety and purity standards as required by FDA Office of Biologics standards.

Biological material should be extensively dialyzed to remove undesired small molecular weight molecules and/or lyophilized for more ready formulation into a desired vehicle, where appropriate. The active compounds will then generally be formulated for parenteral administration, e.g., formulated for injection via the intravenous, intramuscular, sub-cutaneous, intralesional, or even intraperitoneal routes. The preparation of an aqueous composition that contains an active component or ingredient will be known to those of skill in the art in light of the present disclosure. Typically, such compositions can be prepared as injectables, either as liquid solutions or suspensions; solid forms suitable for use in preparing solutions or suspensions upon the addition of a liquid prior to injection can also be prepared; and the preparations can also be emulsified.

Pharmaceutical forms suitable for injectable use include sterile aqueous solutions or dispersions; formulations including for example, aqueous propylene glycol; and sterile powders for the extemporaneous preparation of sterile injectable solutions or dispersions. In all cases the form must be sterile and must be fluid. It must be stable under the conditions of manufacture and storage and must be preserved against the contaminating action of microorganisms, such as bacteria and fungi.

Solutions of the active compounds as free base or pharmacologically acceptable salts can be prepared in water suitably mixed with a surfactant, such as hydroxypropylcellulose. Dispersions can also be prepared in glycerol, liquid polyethylene glycols, and mixtures thereof and in oils. Under ordinary conditions of storage and use, these preparations contain a preservative to prevent the growth of microorganisms.

A therapeutic agent can be formulated into a composition in a neutral or salt form. Pharmaceutically acceptable salts, include the acid addition salts (formed with the free amino groups of the protein) and which are formed with inorganic acids such as, for example, hydrochloric or phosphoric acids, or such organic acids as acetic, oxalic, tartaric, mandelic, and the like. Salts formed with the free carboxyl groups can also be derived from inorganic bases such as, for example, sodium, potassium, ammonium, calcium, or ferric hydroxides, and such organic bases as isopropylamine, trimethylamine, histidine, procaine and the like. In terms of using peptide therapeutics as active ingredients, the technology of U.S. Pat. Nos. 4,608,251; 4,601,903; 4,599,231; 4,599,230; 4,596,792; and 4,578,770, each incorporated herein by reference, may be used.

Carrier can also be a solvent or dispersion medium containing, for example, water, ethanol, polyol (for example, glycerol, propylene glycol, and liquid polyethylene glycol, and the like), suitable mixtures thereof, and vegetable oils. The proper fluidity can be maintained, for example, by the use of a coating, such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

Sterile injectable solutions are prepared by incorporating the active compounds in the required amount in the appropriate solvent with various of the other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof. The preparation of more, or highly, concentrated solutions for direct injection is also contemplated, where the use of DMSO as solvent is envisioned to result in extremely rapid penetration, delivering high concentrations of the active agents to a small area.

Upon formulation, solutions will be administered in a manner compatible with the dosage formulation and in such amount as is therapeutically effective. The formulations are easily administered in a variety of dosage forms, such as the type of injectable solutions described above, but drug release capsules and the like can also be employed.

For parenteral administration in an aqueous solution, for example, the solution should be suitably buffered if necessary and the liquid diluent first rendered isotonic with sufficient saline or glucose. These particular aqueous solutions are especially suitable for intravenous, intramuscular, subcutaneous and intraperitoneal administration. In this connection, sterile aqueous media that can be employed will be known to those of skill in the art in light of the present disclosure. For example, one dosage could be dissolved in 1 ml of isotonic NaCl solution and either added to 1000 ml of hypodermoclysis fluid or injected at the proposed site of infusion.

The term "unit dose" refers to physically discrete units suitable for use in a subject, each unit containing a predetermined quantity of the therapeutic composition calculated to produce the desired responses, discussed above, in association with its administration, i.e., the appropriate route and treatment regimen. The quantity to be administered, both according to number of treatments and unit dose, depends on the subject to be treated, the state of the subject and the protection desired. The person responsible for administration will, in any event, determine the appropriate dose for the individual subject.

The active therapeutic agents may be formulated within a mixture to comprise about 0.0001 to 1.0 milligrams, or about 0.001 to 0.1 milligrams, or about 0.1 to 1.0 or even about 10 milligrams per dose or so. Multiple doses can also be administered, daily, weekly, bi-weekly or monthly for example.

In addition to the compounds formulated for parenteral administration, such as intravenous or intramuscular injection, other pharmaceutically acceptable forms include, e.g., tablets or other solids for oral administration; liposomal formulations; time release capsules; and any other form currently used.

One may also use nasal solutions or sprays, aerosols or inhalants in the present invention. Nasal solutions are usually aqueous solutions designed to be administered to the nasal passages in drops or sprays. Nasal solutions are prepared so that they are similar in many respects to nasal secretions. Thus, the aqueous nasal solutions usually are isotonic and slightly buffered to maintain a pH of 5.5 to 6.5. In addition, antimicrobial preservatives, similar to those used in ophthalmic preparations, and appropriate drug stabilizers, if required, may be included in the formulation.

Additional formulations which are suitable for other modes of administration include suppositories and pessaries. A rectal pessary or suppository may also be used. Suppositories are solid dosage forms of various weights and shapes, usually medicated, for insertion into the rectum or the urethra. After insertion, suppositories soften, melt or dissolve in the cavity fluids. In general, for suppositories, traditional binders and carriers may include, for example, polyalkylene glycols or triglycerides; such suppositories may be formed from mixtures containing the active ingredient in the range of 0.5% to 10%, preferably 1% 2%.

Oral formulations include such normally employed excipients as, for example, pharmaceutical grades of mannitol, lactose, starch, magnesium stearate, sodium saccharine, cellulose, magnesium carbonate and the like. These compositions take the form of solutions, suspensions, tablets, pills, capsules, sustained release formulations or powders. In certain defined embodiments, oral pharmaceutical compositions will comprise an inert diluent or assimilable edible carrier, or they may be enclosed in hard or soft shell gelatin capsule, or they may be compressed into tablets, or they may be incorporated directly with the food of the diet. For oral therapeutic administration, the active compounds may be incorporated with excipients and used in the form of ingestible tablets, buccal tablets, troches, capsules, elixirs, suspensions, syrups, wafers, and the like. Such compositions and preparations should contain at least 0.1% of active compound. The percentage of the compositions and preparations may, of course, be varied and may conveniently be between about 2 to about 75% of the weight of the unit, or preferably between 25-60%. The amount of active compounds in such therapeutically useful compositions is such that a suitable dosage will be obtained.

The tablets, troches, pills, capsules and the like may also contain the following: a binder, as gum tragacanth, acacia, cornstarch, or gelatin; excipients, such as dicalcium phosphate; a disintegrating agent, such as corn starch, potato starch, alginic acid and the like; a lubricant, such as magnesium stearate; and a sweetening agent, such as sucrose, lactose or saccharin may be added or a flavoring agent, such as peppermint, oil of wintergreen, or cherry flavoring. When the dosage unit form is a capsule, it may contain, in addition to materials of the above type, a liquid carrier. Various other materials may be present as coatings or to otherwise modify the physical form of the dosage unit. For instance, tablets, pills, or capsules may be coated with shellac, sugar or both. A syrup of elixir may contain the active compounds sucrose as a sweetening agent methyl and propylparabens as preservatives, a dye and flavoring.

In one embodiment, doses may be given once or more daily, weekly, monthly or yearly, or even once every 2 to 5 or more years. Persons of ordinary skill in the art may estimate repetition rates for dosing based on measured residence times and concentrations of the targetable construct or complex in bodily fluids or tissues. Following successful treatment, it may be desirable to have the patient undergo maintenance therapy to prevent the recurrence of the disease state, wherein the therapeutic agent is administered in maintenance doses, ranging from 0.01 ug to 100 mg per kg of body weight, once or more daily, to once every 5 years.

In another embodiment, a particular dose may be calculated according to the approximate body weight or surface area of the patient. Other factors in determining the appropriate dosage can include the disease or condition to be treated or prevented, the severity of the disease, the route of administration, and the age, sex and medical condition of the patient. Further refinement of the calculations necessary to determine the appropriate dosage for treatment is routinely made by those skilled in the art, especially in light of the dosage information and assays disclosed herein. The dosage can also be determined through the use of known assays for determining dosages used in conjunction with appropriate dose-response data.

Kits

Some embodiments concern kits for compositions and methods disclosed herein. A kit can include, but is not limited to, one or more compositions in one or more containers or vessels for reducing, inhibiting, treating and/or preventing CaMKII activity (e.g. for reducing neuronal cell death or inhibiting a neurodegenerative disorder). Alternatively, a kit may include only reagents, CaMKIIN derived molecules or constructs for further research of potency on inhibiting CaMKII activity or other activity. In addition, kits are contemplated of use for health professionals in treating disorders and conditions indicated herein.

EXAMPLES

Embodiments herein are further illustrated by the following examples and detailed protocols. However, the examples are merely intended to illustrate embodiments and are not to be construed to limit the scope herein. The contents of all references and published patents and patent applications cited throughout this application are hereby incorporated by reference.

Example 1

In certain exemplary methods, portions or peptides of CaM-KIIN are generated. In certain examples, peptides are 21 amino acids in length. As represented in FIG. 1. CN21a (CN) contains full CaMKII inhibitory potency and specificity of CaM-KIINtide. FIG. 1A represents CN peptides relative to the sequence of CaM-KIINtide, termed CN27. Darker bars indicate greater CaMKII inhibitory potential found in this study. In FIG. 1B, CN21a contains the full inhibitory potency. Deletion of the 3 N-terminal amino acids of CN21a abolishes inhibition, while C-terminal deletion reduces it. In another example, $Ca^{2+}$/CaM-induced CaMKII activity was measured by $^{32}P$ incorporation into the peptide substrate AC2. In FIG. 1C, CN21a specificity was tested on a panel of different kinases (at 5 µM, 50-fold IC50). Kinase activity without inhibitor was normalized to 100% for each kinase. CaMKII activity was completely blocked, while activities of the other kinases were not affected. Individual data points of duplicate assays are shown. In FIG. 1D, CN27 and CN21 were demonstrated to inhibit both major brain CaMKII isoforms, α and β. Error bars indicate s.e.m.

Figure 2B:
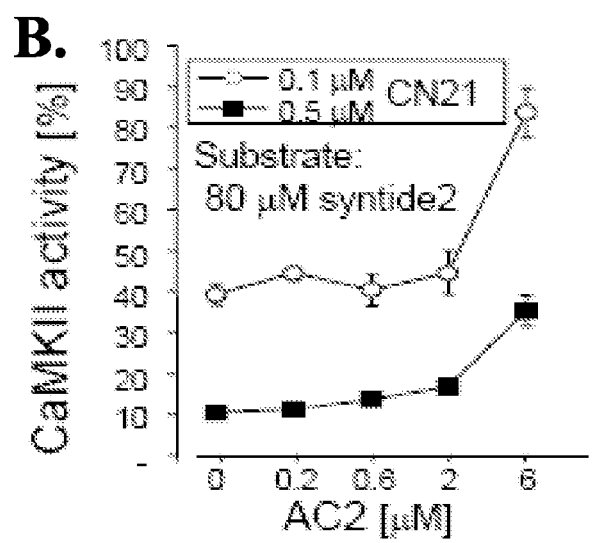
Figure 2C:
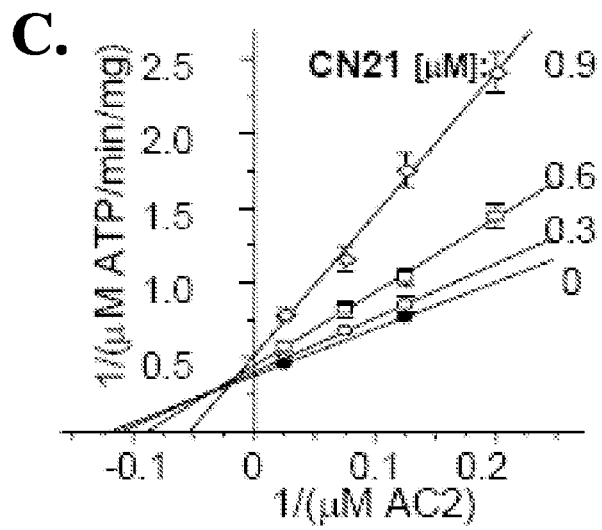

In another exemplary experiment, CNs were demonstrated to differentially inhibit phosphorylation of two peptide substrates (see FIGS. 2A-2C). In one example, FIG. 2A represents that CN peptides (e.g. 1 µM) block CaMKII phosphorylation of the peptide substrate syntide2 (derived from a phosphorylation site on glycogen synthase), but only reduce phosphorylation of AC2 (derived from the auto-phosphorylation site around T286). FIG. 2B represents that AC2 interferes with CaMKII inhibition by CN21. Kinase assays were done in presence of 0.1 or 0.5 µM CN21 with 80 µM syntide2 as the principle substrate; AC2 was added at the indicated concentration. Kinase activity is shown as % of maximal activity without CN21 peptide. Error bars indicate s.e.m. Inhibition by CN21 is competitive with AC2, demonstrated in FIG. 2C. Standard kinase assays were performed with 10 nM CaMKII, 1 µM CaM, and varying concentrations of AC2 (40, 13.33, 8, and 5 µM) and CN21 (0, 0.3, 0.6, and 0.9 µM). In a Lineweaver-Burk plot, increasing the CN21 concentration has a much stronger effect on apparent $-1/k_m$ (x-axis intersection) than on apparent $1/v_{max}$ (y-axis intersection), indicating inhibition by a largely competitive mechanism. The $r^2$ values of regression for all inhibitor series were >0.994.

Figure 3A:
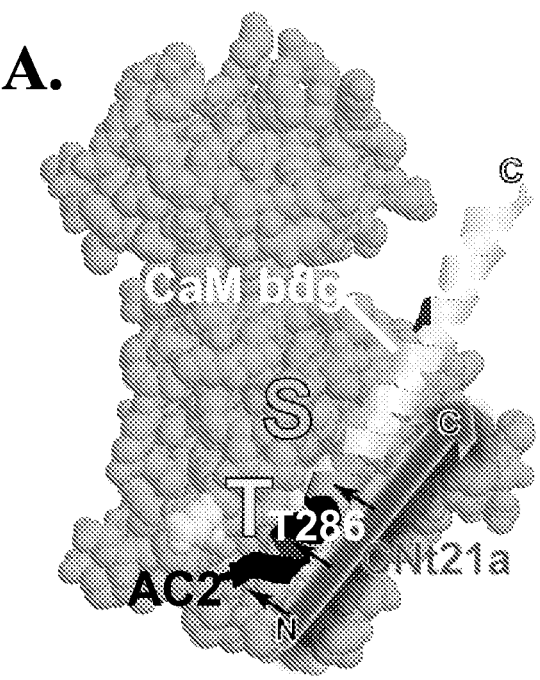
FIGS. 3A-3C represent interactions of CaM-KIIN and CN21 with respect to CaMKII T-site. 3A represents a molecular model of a CaMKII kinase domain with some of the proposed associating molecules identified. 3B represents a histogram of a comparison to GFP-CaMKIIα wild type. 3C represents a Western blot analysis of $Ca^{2+}$/CaM-induced CaMKII binding to immobilized GST-NR2B-c.
Figure 3B:
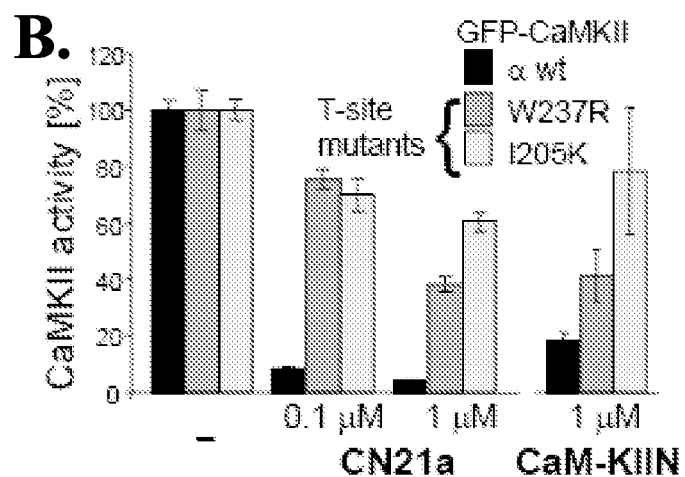
Figure 3C:
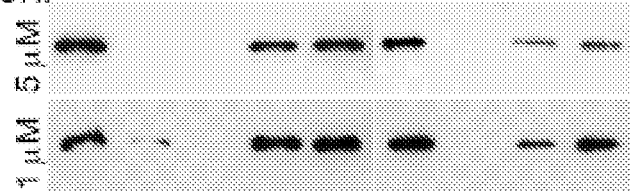

In another example, FIG. 3. CaM-KIIN and CN21 have been demonstrated to interact with the CaMKII T-site. FIG. 3A represents a model of CaMKII kinase domain (Rosenberg et al., 2005) with the substrate binding S-site (indicated), the T286-region binding T-site (indicated), and the regulatory region (shown as ribbon). The arrow indicates the proposed orientation of CN21a binding to the T-site, when the regulatory region is displaced after activation. FIG. 3B represents a comparison to GFP-CaMKIIα wild type (wt), the activity of the CaMKII T-site mutants W237R and I205K were significantly less affected by CN21a (p<0.001; n=6) or CaM-KIIN (p<0.02; n=4), as assessed by standard kinase assays with the peptide substrate syntide2. Results are normalized to maximal kinase activity without inhibitor. Error bars show s.e.m. FIG. 3C represents an illustration demonstrating that CN21 efficiently blocked $Ca^{2+}$/CaM-induced CaMKII binding to immobilized GST-NR2B-c, an interaction that occurs at the CaMKII T-site. Bound CaMKII was eluted and detected by Western blot. C- but not N-terminal truncations of CN21 also inhibited binding to NR2B.

Figure 4:
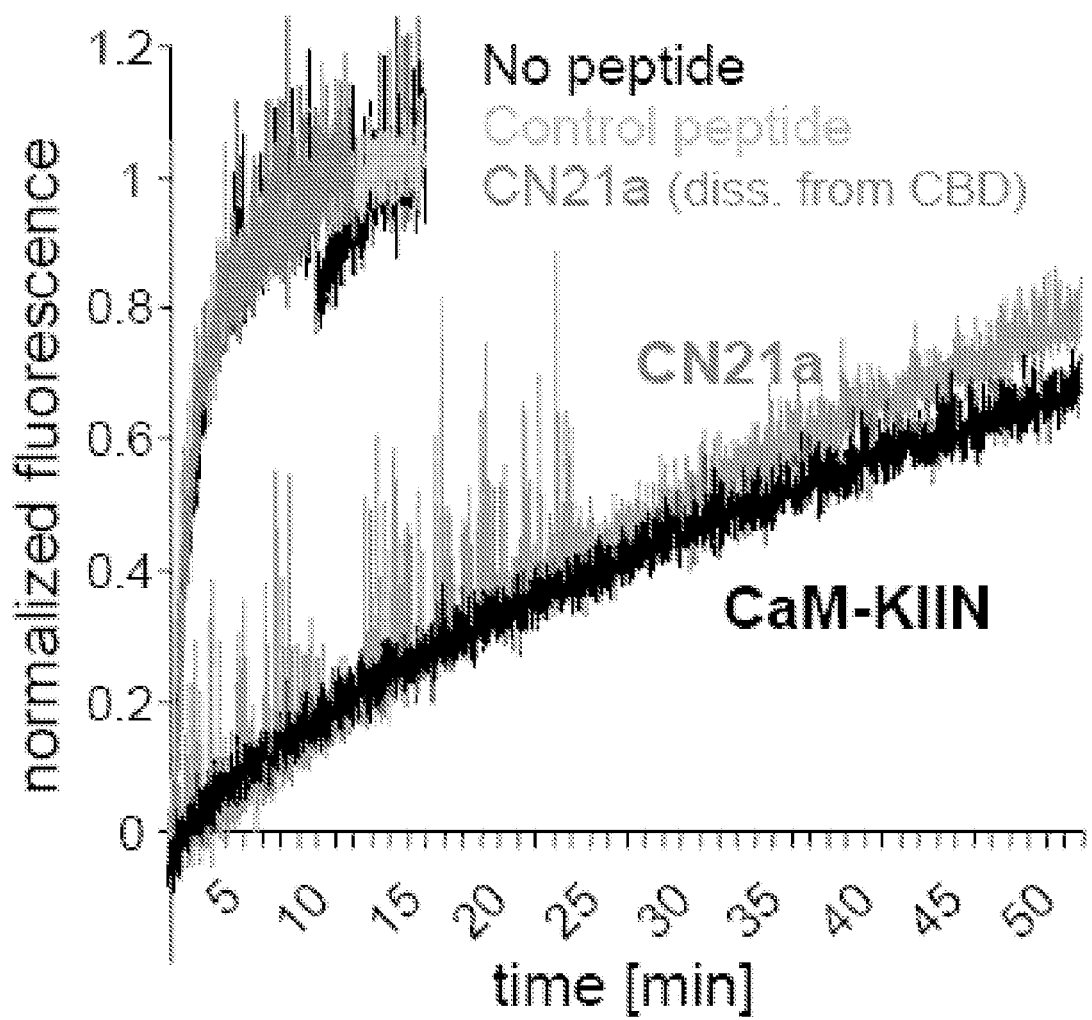
FIG. 4 represents an exemplary plot representing CaM dissociation from CaMKII.

FIG. 4 illustrates an experiment demonstrating that CaM-KIIN and CN21a (5 µM) slowed down CaM dissociation from CaMKII (150 nM). Dissociation of TA-CaM (30 nM) was monitored by its increased fluorescence (1 sec sample times) during a chase with excess unlabeled CaM (60 µM). The control peptide CN21c did not slow down dissociation. CN21a slowed dissociation from CaMKII, but not from a peptide derived from the CaMKII CaM-binding domain (CBD), demonstrating a CaMKII directed effect.

Figures 5A, 5B, 5C:
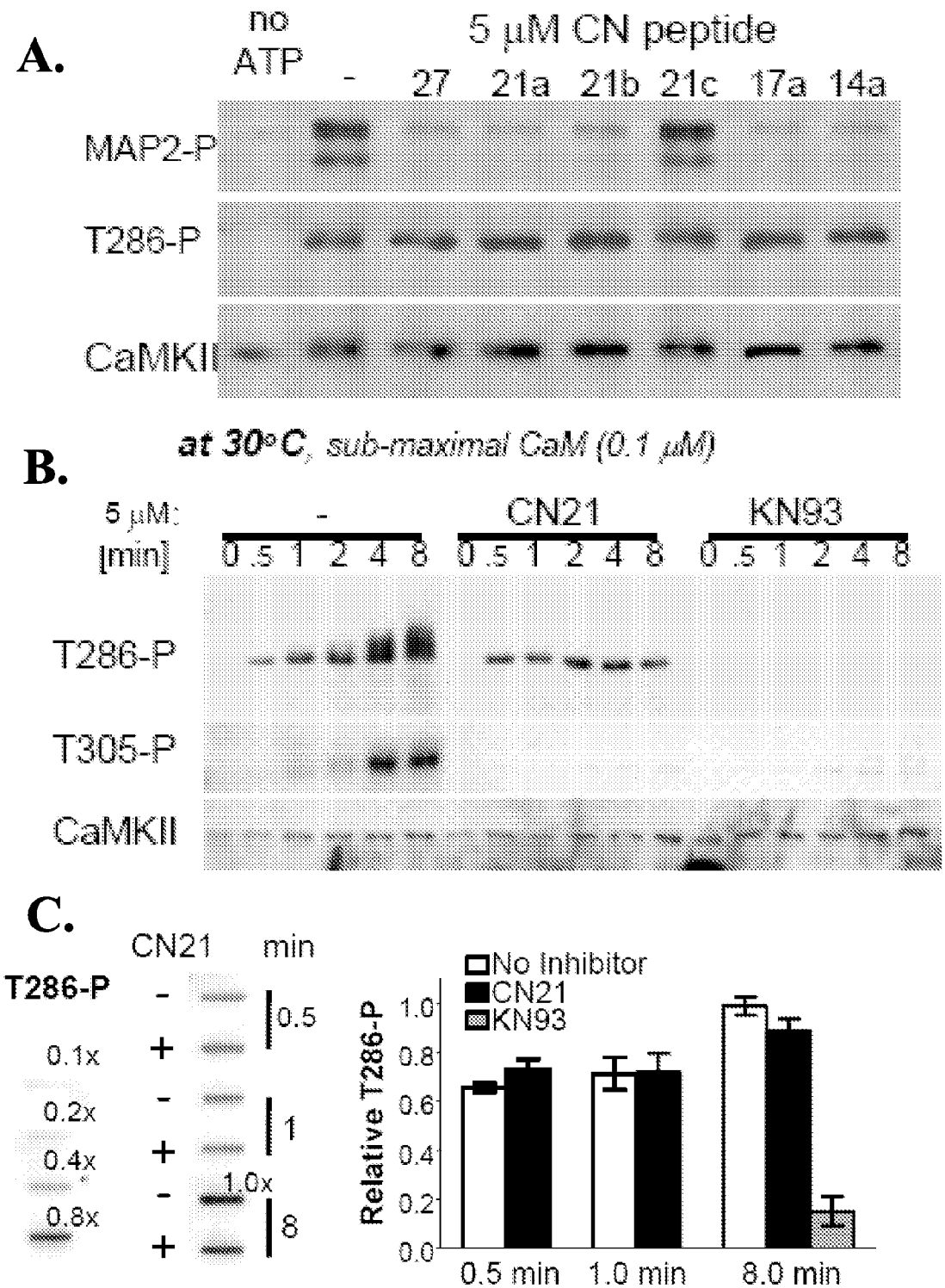
FIGS. 5A-5D represent exemplary results of whether CaMKII autophosporylation can be blocked by CaM-KIIN or CN21. 5A-5C represent exemplary gels indicating that CaM-KIIN and CN21 block substrate- and T305 but not T286 auto-phosphorylation. 5A represents an exemplary gel illustrating that CN peptides blocked CaMKII substrate. 5B represents an exemplary gel of a time course of CaMKII auto-phosphorylation. 5C represents a slot-blot analysis (left panel) was performed for quantification represented in a histogram plot (right panel). 5D represents an exemplary mobility shift gel.
Figure 5D:
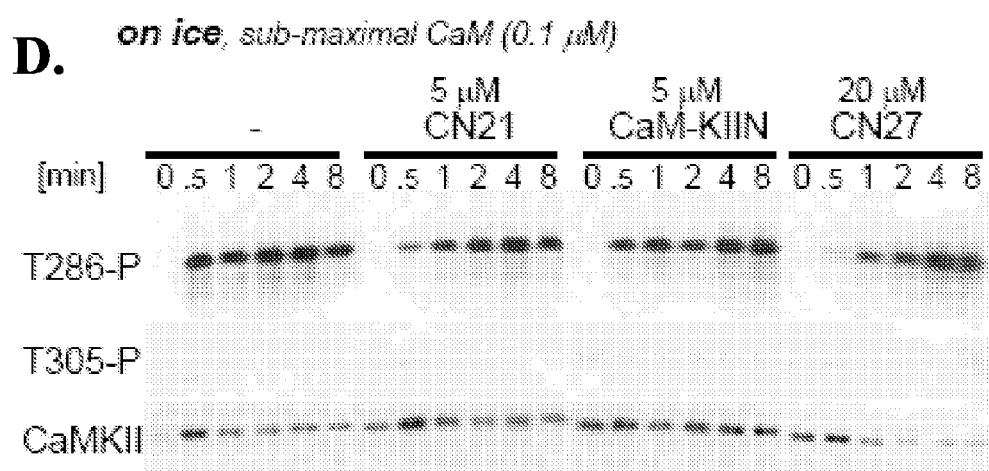

Other experiments were performed to assess whether CaMKII autophosporylation was blocked by CaM-KIIN or CN21. FIGS. 5A-5C illustrate exemplary gels that CaM-KIIN and CN21 block substrate- and T305 but not T286 auto-phosphorylation. FIG. 5A represents CN peptides (5 µM) blocked CaMKII substrate- but not T286 auto-phosphorylation when stimulated with 1 µM CaM (5 min reaction time). Phosphorylation of MAP2 and CaMKII autophosphorylation at T286 were assessed by Western-analysis. Only CN21c failed to block MAP2 phosphorylation, indicating CN21a amino acids 4-14 as core inhibitory region. Importantly, none of the CN peptides blocked CaMKII T286 auto-phosphorylation. FIG. 5B represents a time course of CaMKII auto-phosphorylation stimulated by 0.1 µM CaM at 30° C. CN21 and KN93 (5 and 10 µM, respectively) blocked T305 and other auto-phosphorylation that result in a band-shift of CaMKII. By contrast, T286 was essentially completely blocked by KN93, but not by CN21. Total CaMKII and auto-phosphorylation at T286 and T305 were detected by Western-analysis. FIG. 5C represents a slot-blot analysis (left panel) was performed for quantification (right panel) of T286-auto-phosphorylation in the experiment shown in B. T286 auto-phosphorylation was normalized to the degree seen after 8 min reaction without inhibitor; dilutions of this reaction were used as standard. Slot-blot avoids differences in the area of signal cause by the band-shift seen only in absence of inhibitor. CN21 had no significant effect on the T286-auto-phosphorylation measured (p>0.25). Error bars show s.e.m. of triplicates. FIG. 5D represents where reactions as in B (submaximal CaM), were slowed down further by low temperature (on ice). Under these conditions, CN inhibitors slowed down T286 auto-phosphorylation, but still did not completely block it. T305 and other auto-phosphorylation that result in band shift were not detected under these conditions.

Figure 6A:
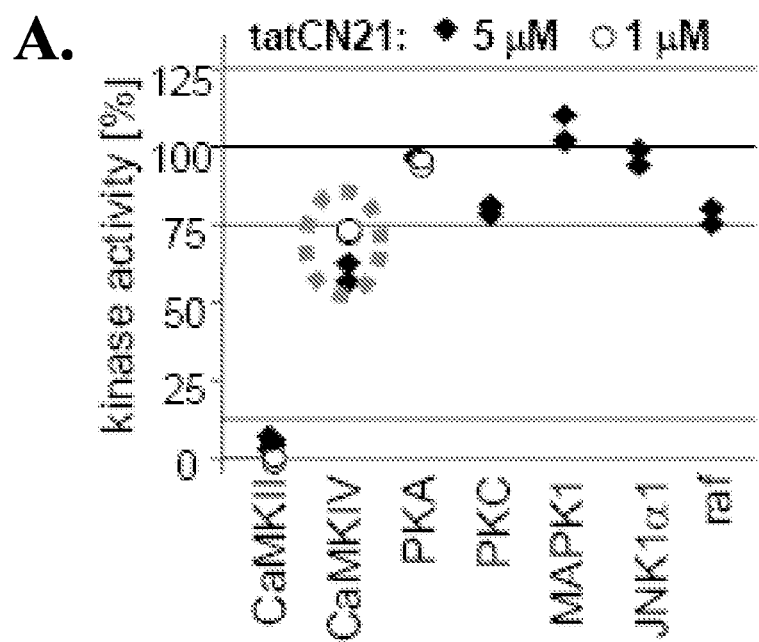
FIGS. 6A-6B represent an exemplary construct of a CaMKIIN derived molecule, CN21 linked to tat, termed tatCN21. 6A illustrates the effect of tatCN21 on a panel of different kinases. 6B illustrates an exemplary Western blot of CaMKII binding.
Figure 6B:
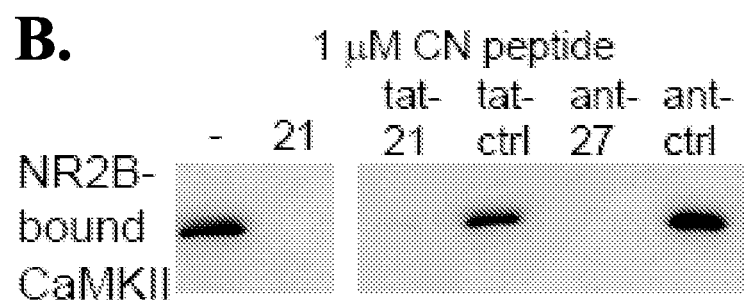

In another exemplary method, a construct was made where a portion of a CaMKIIN molecule, CN21 was made more cell penetrating. This molecule is referred to as tatCN21. tatCN21 was demonstrated to retain inhibition of CaMKII activity and binding to NR2B. FIG. 6A illustrates the effect of tatCN21 on a panel of different kinases. Kinase activity without inhibitor was normalized to 100% for each kinase. 1 µM tatCN21 completely blocked CaMKII activity, while even 5 µM tatCN21 had little or no effect on the other kinases: a mild but clear effect was observed only on CaMKIV (~35%). Individual data points of duplicate assays are shown. FIG. 6B illustrates that similar to CN21a, both tatCN21 and antCN27 efficiently blocked $Ca^{2+}$/CaM-induced CaMKII binding to immobilized GST-NR2B-c. Control peptides did not affect CaMKII binding. Bound CaMKII was eluted and detected by Western blot.

Example 2

Figure 7A:
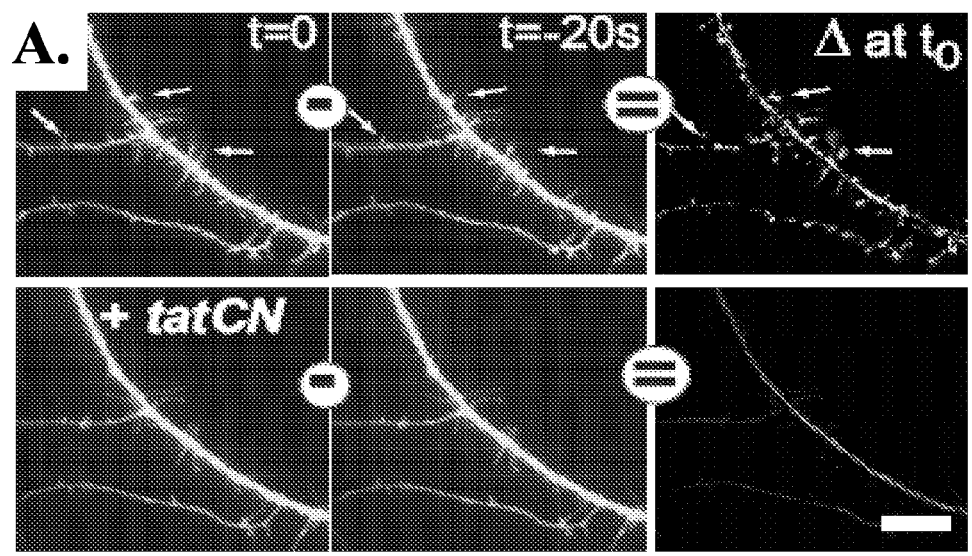
FIGS. 7A-7C represent motility of hippocampal neurons. 7A represents exemplary images of the same dendrite area before and 20 min after addition of tatCN21, at different times of acquisition as indicated. 7B represents average of Δ images in pseudo color visualize motility in a larger area (110×148 μm). 7C represents quantification of a change in motility after application of tatCN21 or tatRev control based on Δ image average projections.
Figure 7B:
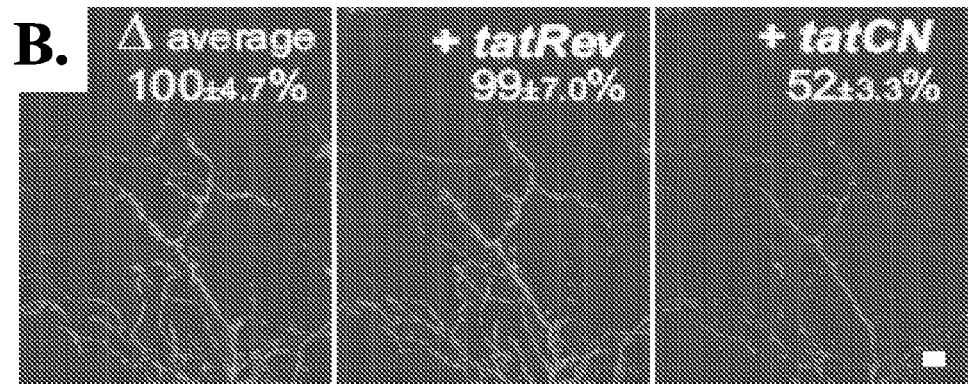
Figure 7C:
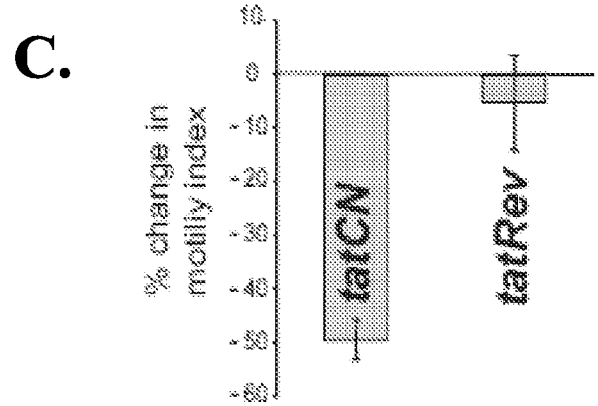

In another example, motility of hippocampal neurons was analyzed. As illustrated in FIG. 7, tatCN21 inhibits motility in hippocampal neurons. Images of GFP expressing hippocampal neurons (5-6 days in vitro) were acquired at 30° C. in 20 s intervals in order to assess motility. After the first set of 16 images, neurons were incubated with tatCN21a or with control peptide for 20 min; then a second set of images was taken. Scale bars: 10 μm. FIG. 7A represents exemplary images of the same dendrite area before and 20 min after addition of tatCN21, at different times of acquisition as indicated. Δ images were created by subtracting pixel intensities of one image from the one taken 20 s later. Shown Δ image intensities are 4fold exaggerated compared to the original captures on the left. FIG. 7B represents average of Δ images in pseudo color visualize motility in a larger area (110×148 μm). Error indicates s.e.m. of the Δ images used for the average projections shown. FIG. 7C represents quantification changes in motility after application of tatCN21 or tatRev control based on Δ image average projections. Error bars show s.e.m. (n=7 neurons from three independent cultures). In three cases, neurons were treated first with tatRev and then tatCN21, as shown in B.

Figure 8:
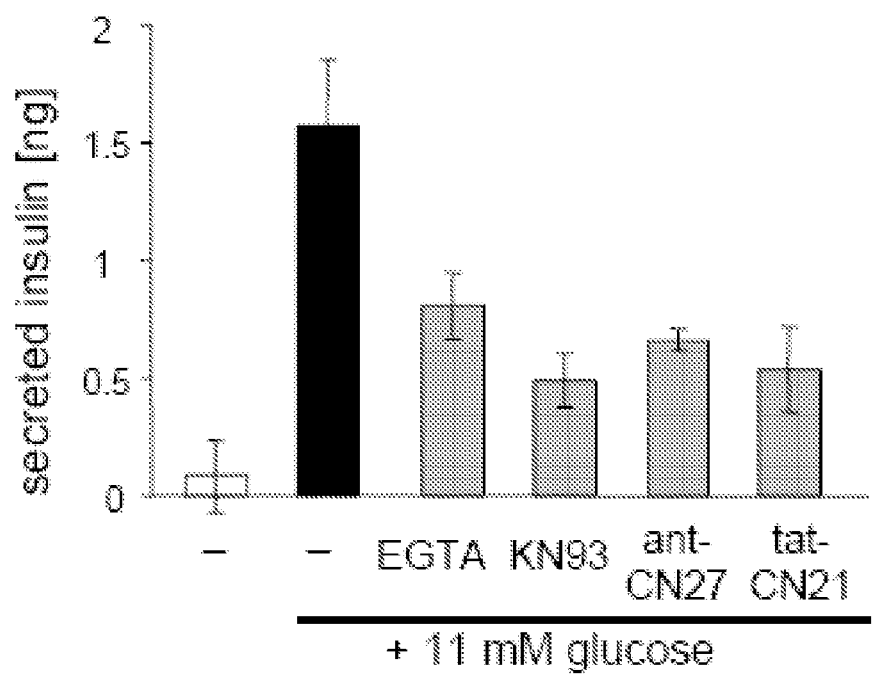
FIG. 8 represents an exemplary histogram illustrating a portion of a CaM-KIIN molecule and its effects on glucose induced insulin secretion.

In another exemplary method, a portion of a CaM-KIIN molecule was examined for effects on glucose induced insulin secretion. FIG. 8 represents that tatCN21 inhibits glucose-induced insulin secretion. Insulin secretion from acutely isolated rat Langerhans' islets (10 per well) was stimulated by 11 mM glucose. This secretion was inhibited by extracellular EGTA (0.5 mM; instead of 2.5 mM $CaCl_2$), KN93 (10 μM), antCN27 (5 μM) and tatCN21 (5 μM) (p<0.025; for KN93 and tatCN21 p<0.01). Error bars show s.e.m. (n=4; for antCN27 n=3). The CN peptides inhibited secretion also in an independent experiment (which did not include the standard for determining absolute insulin amount; not shown).

In certain exemplary methods, peptides and even proteins can be made cell-penetrating by fusion to the arginine/lysine-rich ant or tat sequences (FIG. 9A), providing powerful tools for studying cellular functions. A concern usually tested for is the possibility that fusion may disrupt activity of the original compound. Here, we provide a cautionary tale that any ant fusion can also generate new undesired effects by direct binding to calmodulin (CaM).

In another exemplary method, a fusion molecule was linked to CN. In this example, ant fusion was performed to CaMKIIN inhibitory region (CN; FIG. 9A) in order to generate a potent cell-permeable CaMKII inhibitor, antCN27. Here, ant but not tat fusion with CN peptides generated an additional CaM-directed mode of inhibition (FIGS. 9B and 9C) that compromised specificity (FIG. 9D). The CaM-directed mode but not the CaMKII-specific mode of inhibition was also shared by the reverse sequence control peptide antRev (FIG. 9B). Tat fusion to the newly identified minimal inhibitory region of CaM-KIIN, CN21, did not show the CaM-directed mode of inhibition (FIG. 9C) and largely retained the specificity of non-fused CN21 (FIG. 9D). CN peptides efficiently block substrate- and T305 but not T286 auto-phosphorylation of CaMKII (however, the autonomous activity generated by the T286 auto-phosphorylation is blocked by CN peptides). The tat fusion peptides showed the same differential effect on substrate versus T286 phosphorylation as non-fused CNs, whereas ant fusion peptides additionally inhibited T286 auto-phosphorylation by their CaM-directed mode (FIG. 10). Both ant- and tat-fused CNs blocked CaMKII binding to NR2B.

Figure 9F:
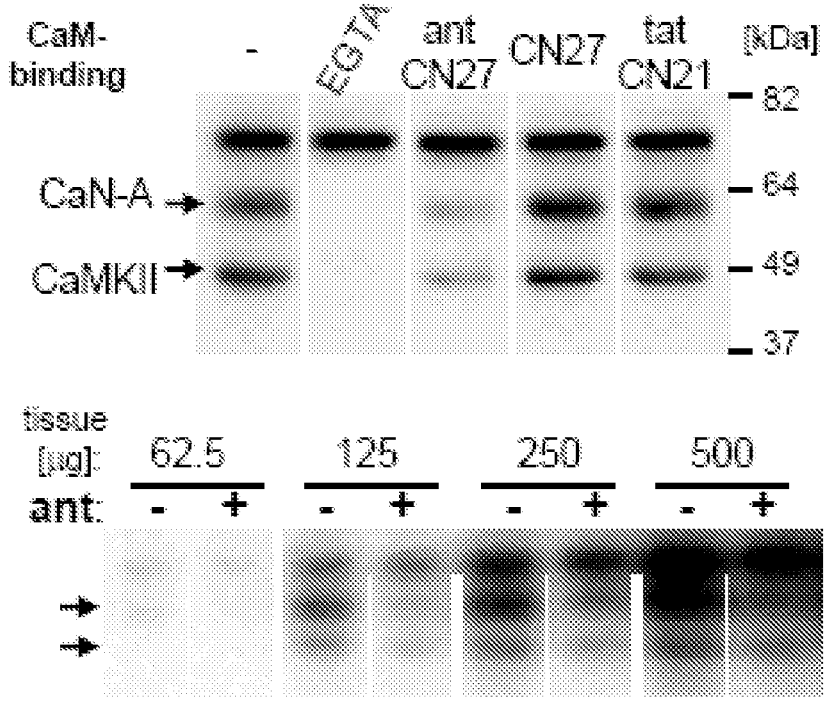
Figure 9G:
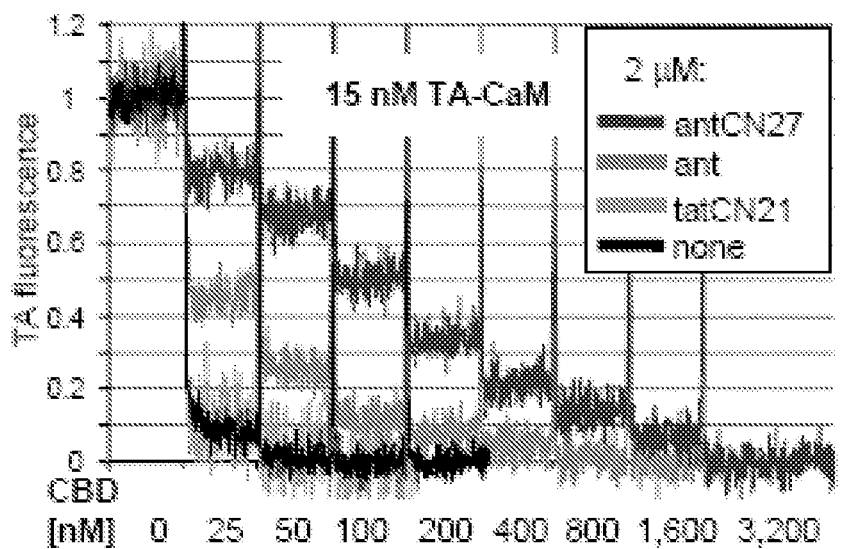
Figure 10:
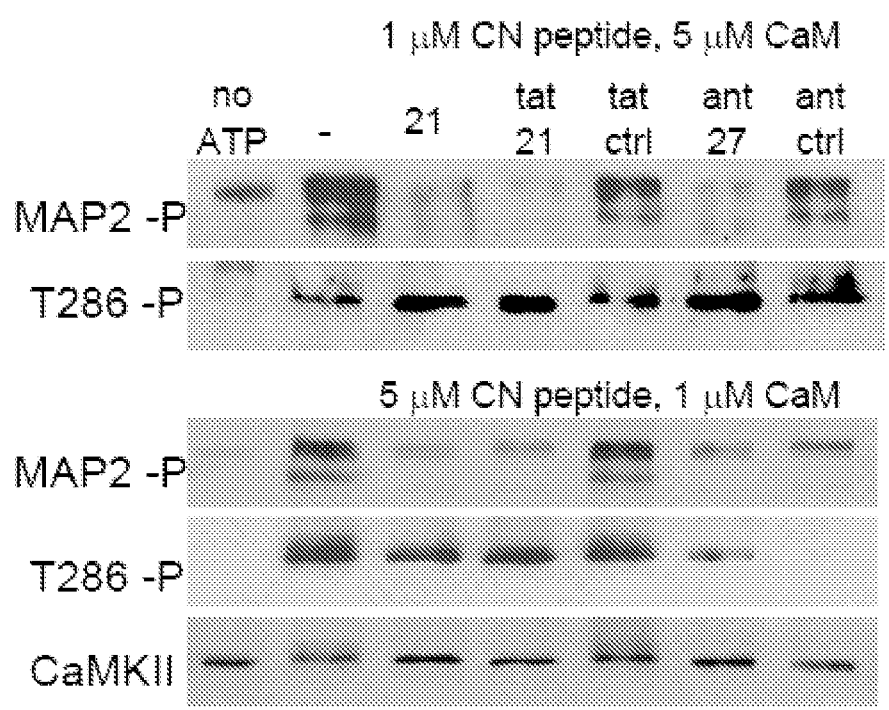
FIG. 10 illustrates exemplary gel analysis of a differential effect of tat- and ant-CN fusion peptides on CaMKII substrate- and auto-phosphorylation.

Direct binding of biotinylated CaM to ant immobilized by slot blot revealed the mechanism of the CaM-directed mode of inhibition (FIG. 9E). Formally, the ant peptides competed with CaMKII for CaM binding. CaM did not bind to the tat sequence or the non-fused CN peptides (FIG. 9E). In an overlay assay, biotinylated CaM bound to calcineurin A (CaN-A), CaMKIIa, and other proteins from rat brain extract immobilized on PVDF membranes (FIG. 9F). The ant fusion peptides interfered with $Ca^{2+}$-dependent CaM binding, whereas tat fusion peptides and non-fused CN peptides did not (FIG. 9F). The ant peptide alone also interfered with such CaM binding, but somewhat less efficiently than antCN27 (FIG. 9F). No significant interference with $Ca^{2+}$-independent binding of CaM was observed. TA-labeled CaM represents reduced fluorescence after binding to CaMKII or its CaM binding domain (CBD; ~0.05 nM $k_D$ for $CaM^5$; see also FIG. 9G). Surprisingly, binding to ant did not reduce TA-CaM fluorescence, preventing direct affinity measurement, but enabling competition experiments (FIG. 9G). Competition with CBD indicated ~1 nM and ~5 nM $k_D$ of antCN27 and ant for binding to CaM, respectively, while tatCN21 did not show any competition (FIG. 9G).

Furthermore, motility was affected only by antCN27 but not antRev, which shares the CaM-directed but not CaMKII-specific mode of inhibition (FIG. 9B). Results show that ant binding to CaM can be enhanced even by fusion to peptides that do not detectably interact with CaM on their own (FIGS. 9E and 9G). Here, tat fusion provided a viable alternative for creating a potent, specific, and cell-permeable CaMKII inhibitor, tatCN21.

Figures 11A, 11B, 11C:
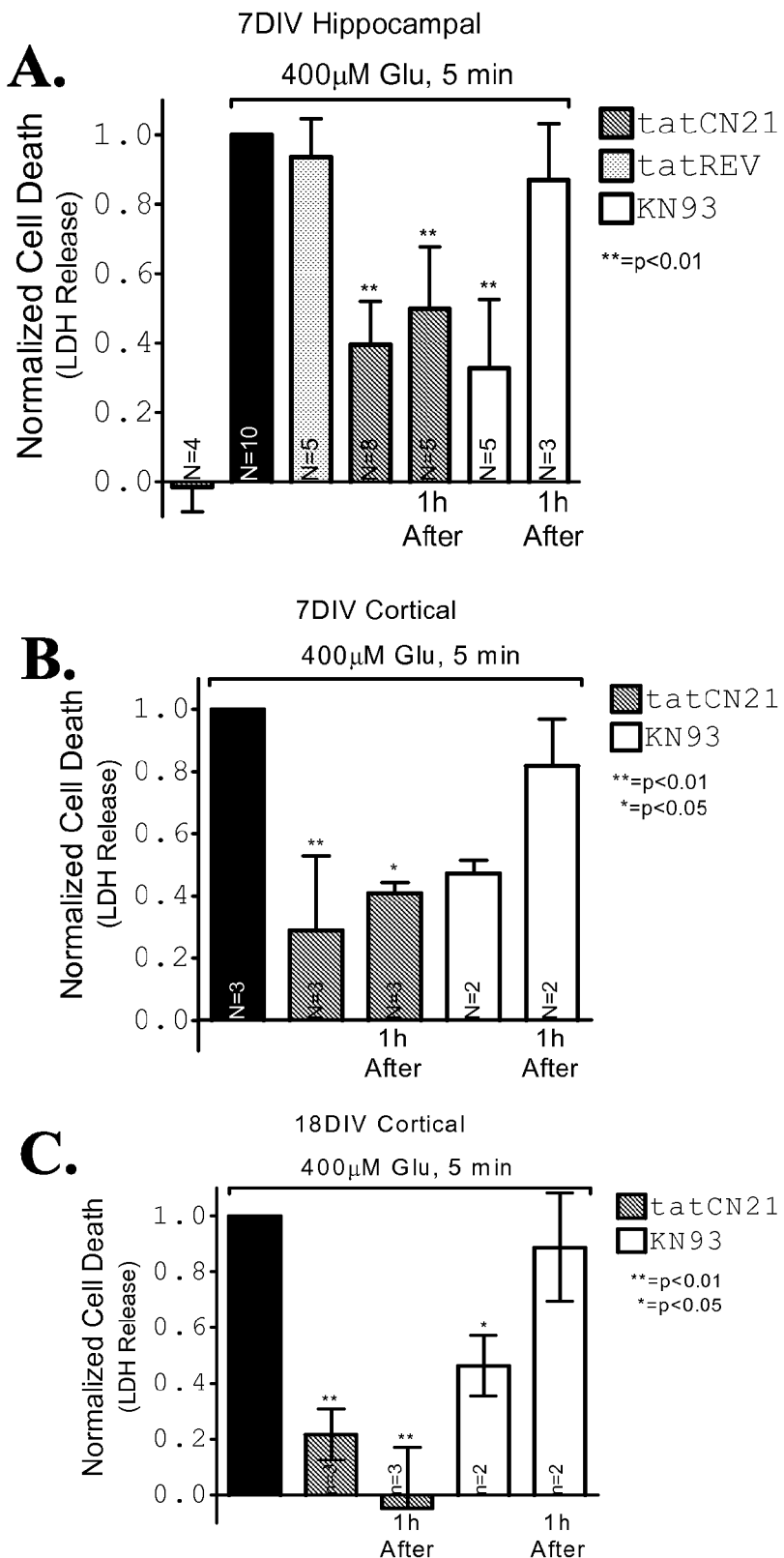
FIGS. 11A-11E represent exemplary histograms of neuronal cell death measured by LDH release. In this exemplary method, glutamate was used to induce neuronal cell death and a construct was analyzed to examine whether it was capable of attenuating neuronal cell death before and after glutamate insult (11A-11E). 11D represents an exemplary histogram of 7DIV cortical up to 6 hours after insult in the presence or absence of tatCN21. 11E represents an exemplary histogram (left panel) illustrating siRNA targeting CaMKIIα (siα) and expression of CaMKII in 10DIV hippocampal neurons as indicated by western-blot (right panel).

FIGS. 9A-9G illustrate that ant but not tat fusion compromised specificity of an inhibitor peptide by direct binding to calmodulin. (9A) The ant and tat sequences fused to the N-terminus of CNs; (K) was replaced by the first K of CNt in the fusion, (9B) Extent of CaMKII inhibition by 1 u,M antCN27 and the reverse sequence control antRev depended on the CaM concentration, indicating an additional CaM-directed mode of inhibition generated by ant fusion. Measured was AC2 phosphorylation as described[4]. Error bars show s.e.m. (9C) 1 uM tatCN21 strongly inhibited CaMKII-mediated AC3 phosphorylation at all CaM concentrations, while the reverse and scrambled sequence controls tatRev and tatScr had no effect compared to assays without tat peptide. (9D) antCN27 blocked CaMKII activity, but also affected PKC and reduced CaMKIV activity by ~70%. tatCN21 blocked CaMKII activity at both 1 and 5 u,M, and reduced CaMKIV activity by ~35% only at 5 U.M; other kinases were not affected. Kinase panel assays were done as described, (9E) Binding of biotinylated CaM (25 nM in TBS, pH 7.5, 1 mM $CaCl_2$) to peptides immobilized by slot blot, (9F) Interference of peptides (5 μM) with CaM binding (conditions as in e) to brain proteins in a blot overlay assay. The major $Ca^{2+}$-dependent CaM-binding proteins were Calcineurin A (CaN-A) and CaMKIIoc; additional protein binding was detected after longer exposure (see FIGS. 11A-11B). AntCN27 (upper panel) and ant (lower panel) affect $Ca^{2+}$-dependent CaM binding, but not binding to proteins also detected after $Ca^{2+}$ was chelated by EGTA. (9G) antCN27 and ant, but not tatCN21, compete with the CaMKII CaM-binding domain (CBD) for binding of TA-labeled CaM. Fluorescence of TA-CaM is reduced by binding to CBD. Fluorescence ($A_{ex}$=335 nm; $X_{era}$=415 nm; 1 s sample time) was monitored for 150 s after each addition of CBD as previously described.

FIG. 10 illustrates a differential effect of tat- and ant-CN fusion peptides on CaMKII substrate- and auto-phosphorylation. Reactions were performed in presence of 1 uM CN peptides and 5 uM CaM (upper panels) or 5 uM CN peptides and 1 uM CaM (lower panels), with 20 nM CaMKII and 10 nM MAP2. Phosphorylation of MAP2 and CaMKII T286 auto-phosphorylation were assessed by Western-analysis. tatCN21, but not the tat control peptide, blocked MAP2 but not T286 phosphorylation, as seen for non-fused CN21. Similar results were obtained for the ant peptide pair, but only at low peptide/high CaM concentration. At high peptide/low CaM, both ant peptides interfered with autophosphorylation, as predicted based on their additional CaM-competitive mode of inhibition generated by ant fusion.

Example 3

In another example, neuronal cell death is measured by LDH release. In this exemplary method, glutamate was used to induce neuronal cell death, A portion of CaMKIIN was fused to a cell penetrating molecule to generate tatCN21a construct. The construct was analyzed to examine whether it was capable of attenuating neuronal cell death before and after glutamate insult (see FIGS. 11A-11C). tatCN21a inhibited glutamate induced neuronal cell death not only when present during the insult, but, also when added 1 h after the insult. By contrast, traditional CaMKII inhibitor KN93 was protective only when present during the insult, but not when added after the insult. This demonstrates that the new CN inhibitors described here, but not the traditional KN inhibitors, are useful in a clinically relevant time window. Corresponding results were observed in dissociated cultures of rat hippocampal (FIG. 11A) and cortical (FIGS. 11B-11C) cultures, both after 7 days (FIGS. 11A-11B) and after 18 days (FIG. 11C) in culture.

Figure 11D:
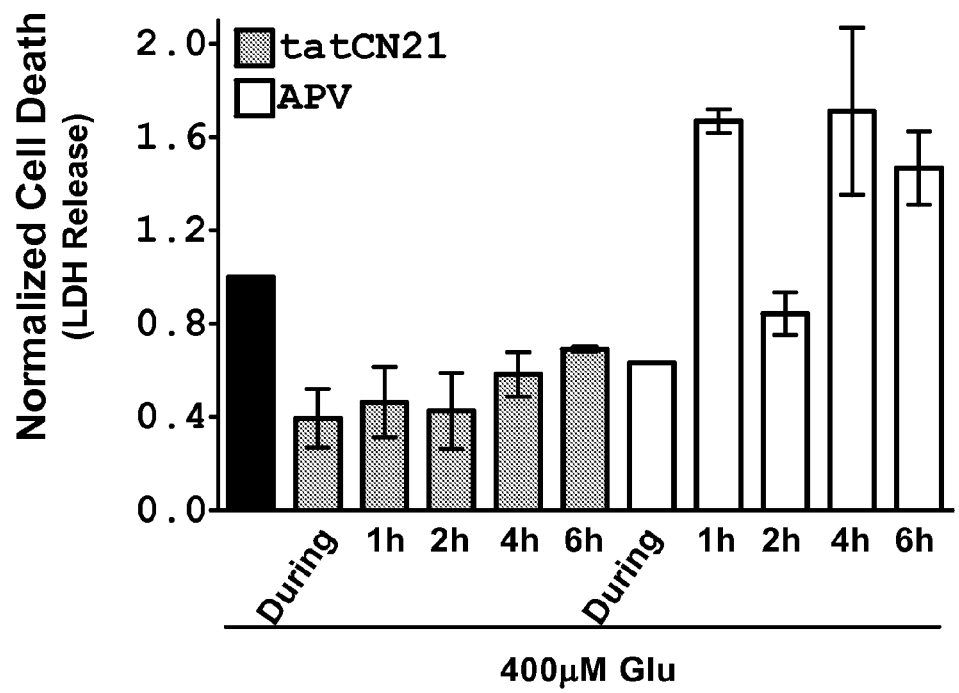

FIG. 11D represents an exemplary histogram illustrating that tatCN21 inhibits glutamate induced cell death (7DIV cortical) when added 1-6 hours post insult, but APV did not. APV, a NMDAR antagonist, only reduces cell death when present during the insult. Like KN93, it is ineffective when added after insult.

Figure 11E:
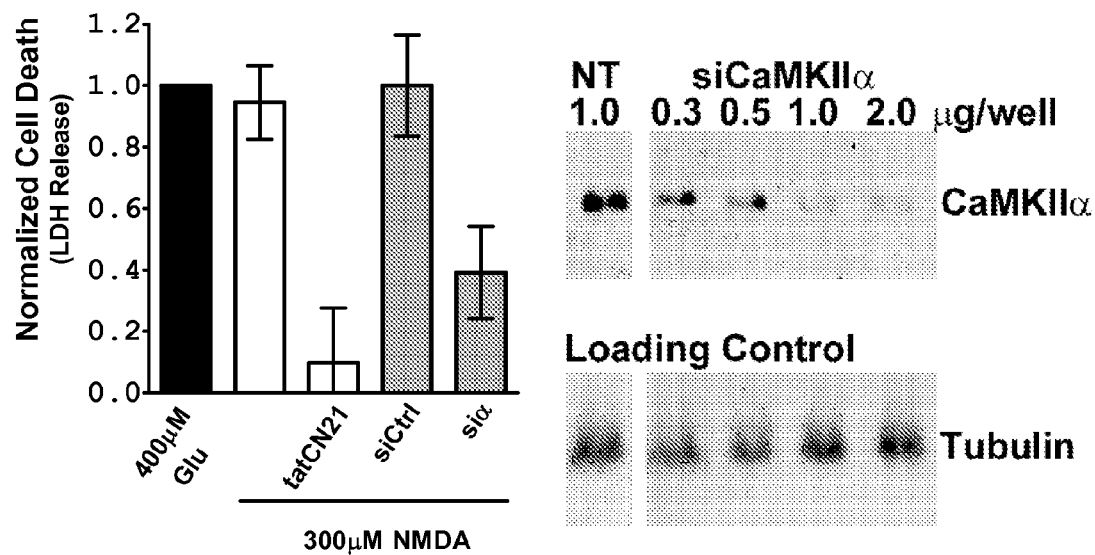

FIG. 11E represents that siRNA targeting CaMKIIα (siα) reduces expression of CaMKII in 10DIV hippocampal neurons as indicated by western-blot. Neurons were co-transfected with siRNA or non-targeting RNA (NT) at 8DIV and were assayed at day 10. Cells transfected at 8DIV with 1-2 mg/well of sia in 24 well plates showed reduced CaMKIIa when assayed at 10DIV by western-blot. Blots were re-probed for tubulin as a loading control. sia and sib reduce NMDA induced cell death in 10DIV hippocampal neurons. Cells were treated with 300 mM NMDA plus 50 mM CNQX (an AMPAR inhibitor) for 5 minutes and cell death was assayed 24 hours after insult. NMDA and CNQX were used because some evidence indicates that knockdown of CaMKII increases gluR1 expression levels and thus might increase AMPAR expression. Increased AMPAR expression is thought to lead to increased cell death. Thus, by inducing cell death with NMDA and an AMPAR inhibitor, the AMPAR component was reduced. Also shown, as control, tatCN21 reduces NMDA-induced cell death in 10DIV hippocampal neurons.

Example 4

FIGS. 12A-12D represent that KN93 and tatCN21 have different effects on CaMKII. FIG. 12A illustrates that both tatCN21 and KN93 inhibit calcium and calmodulin stimulated CaMKII activity, but only tatCN21 inhibits autonomy. Stimulated CaMKII activity was assessed using purified CaMKII, $[\gamma^{32}P]$ATP, and the CaMKII substrate, syntide2. Reaction was initiated by addition of calcium and calmodulin. To measure autonomous activity, CaMKII was pre-autophosphorylated by incubation with calcium and calmodulin, which was then chelated by addition of EDTA prior to adding the kinase to syntide2 and $[\gamma^{32}P]$ATP. FIG. 12B represents self-association in vitro is inhibited by both KN93 and tatCN21. To measure self-association, purified CaMKII was incubated for five minutes with 1 mM ADP, calcium and calmodulin, and the appropriate inhibitor. The reaction mixture was then centrifuged to pellet the self-associated kinase. The supernatant (S) was removed and saved and the pellet (P) was resuspended. Both were then resolved by SDS-PAGE and western-blotted for CaMKII. Self-associated kinase is found in the pellet. FIG. 12C represents binding to the immobilized NR2B subunit of the NMDAR in vitro was determined in the presences or absence of tatCN21, KN93, or a non-specific kinase inhibitor, H7. TatCN21 and KN93 inhibited binding, but H7 did not. FIG. 12D represents a Table summarizing the effects of tatCN21 and KN93 on CaMKII activity, NR2B binding, or self-association.

Example 5

Figure 13A:
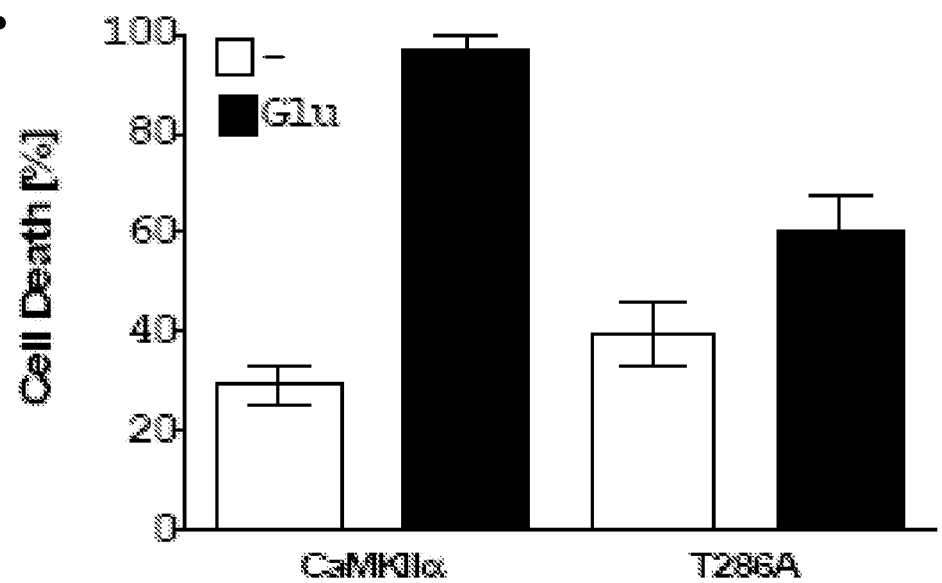
FIGS. 13A-13B represent exemplary histograms of over-expression of T286A and glutamate induced cell death compared with overexpression of CaMKIIa. 13B represents an exemplary histogram of LDH activity in the presence or absence of CaMKII overexpression

FIG. 13A represents that overexpression of T286A reduces glutamate induced cell death compared with overexpression of CaMKIIa. 7DIV hippocampal neurons were transfected with CaMKIIa or T286A, which lacks autonomy. Cell death was assessed by staining with, in this example, Ethidium Homodimer 2

Figure 13B:
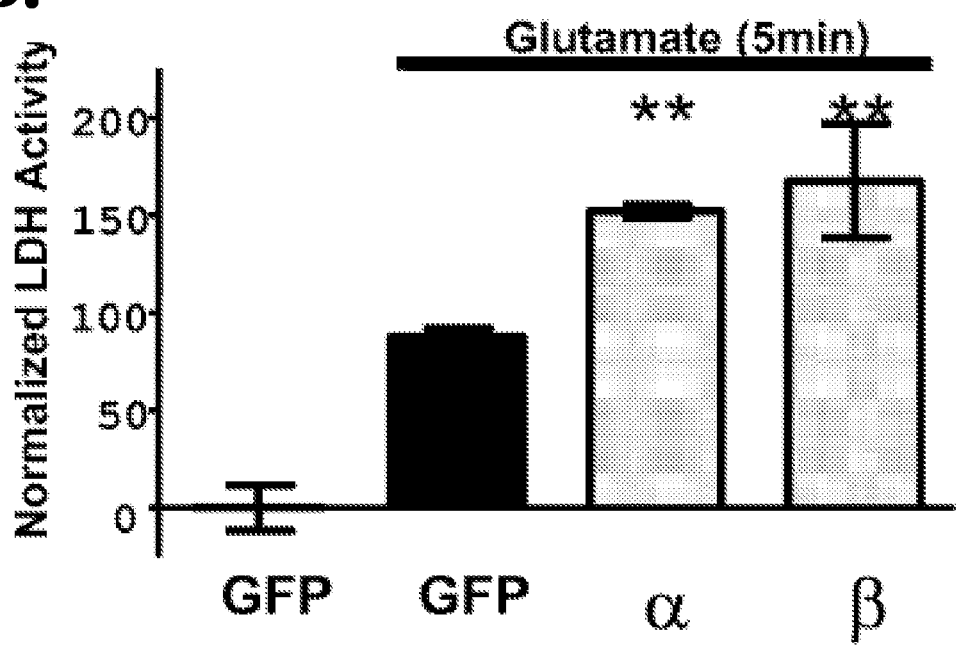

In other correlative experiments, CaMKII overexpression was examined and was found to enhance glutamate-induced neuronal cell death (see FIG. 13B). Neuronal cell death by stroke (and traumatic brain injury, and neurodegenerative diseases) are thought to be caused mainly by "excitotoxcity" (toxic effect of excessive excitatory neurotransmitters, mainly glutamate). This observation is consistent with protective effects observed after CaMKII inhibition. In addition, traditional CaMKII inhibitor KN93 was examined. KN93 protects from glutamate induced neuronal death only when applied during but not after glutamate insult. This is in contrast to a construct of the instant invention, tatCN21, that not only protects during but was also demonstrated to protect after glutamate insult (see FIGS. 11A and 11C). Both inhibitor tatCN21 and a traditional inhibitor (KN93) protected neurons from excitotoxic cell death in culture, at least when present during the glutamate insult (cell death was reduce by half). Remarkably, tatCN21 (but not KN93) was protective also when added 1 h after the insult (and likely up to 4-6 h after). Glutamate has at least four effects on CaMKII (inducing 2 activation states, and 2 forms of translocation), and at least on is affected differently by tatCN21 and KN93: tatCN21 (in contrast to KN93) blocks not only stimulated but also autonomous CaMKII activity (generated by T286 autophosphorylation). Thus, autonomous CaMKII activity is a drug target for therapeutic protection from excitotoxic cell death after an insult. These conclusions based on the inhibitor studies were corroborated by overexpression of CaMKII wild type enhanced neuronal cell death; overexpression of the constitutively autonomous T286 mutant enhanced it even more, while the autonomy-incompetent T286A mutant had little or no effect.

Example 6

Figures 14A, 14B, 14C:
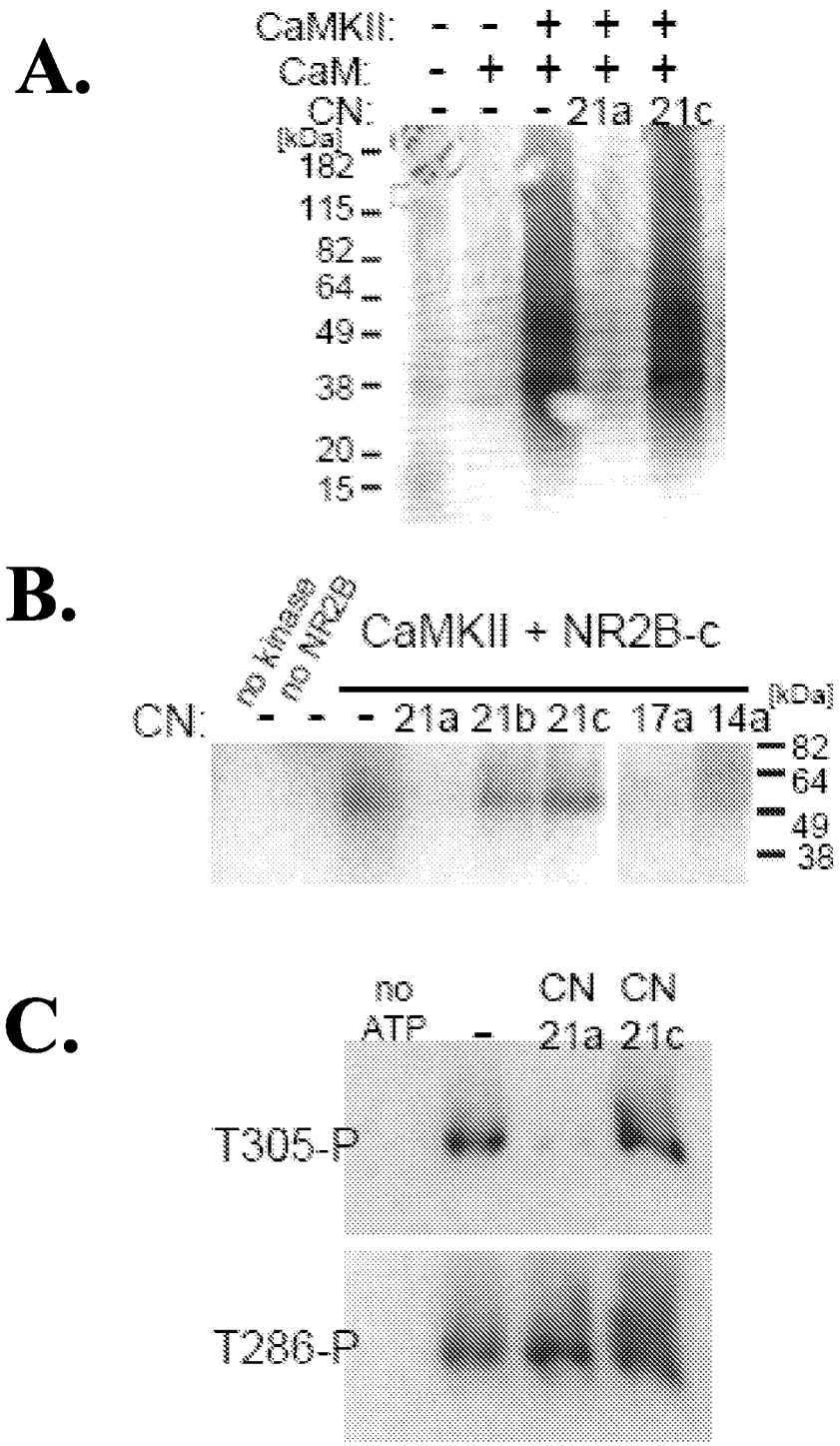
FIGS. 14A-14C illustrates exemplary gel analysis of a minimal inhibitory region of CaM-KIIN for its retention of CaMKII specificity. 14A illustrates an exemplary gel measuring phosphorylation activity in the presence or absence of CN21a. 14B represents an exemplary gel measuring phosphorylation activity in the presence or absence of bacterially expressed GST-NR2B-c (containing C-terminal NR2B amino acid 1,120 to 1,482). 14C represents an exemplary gel measuring autophosphorylation activity using phosphospecific antibodies.

FIGS. 14A-14C illustrates a minimal inhibitory region of CaM-KIIN retains CaMKII specificity. Three overlapping 21 amino acids long peptides were derived from the previously identified inhibitory region of CaM-KIIN (FIG. 1A). Their effect on AC2 substrate phosphorylation by CaMKII was then assayed in vitro (FIG. 1B). The N-terminal peptide CN21a showed the full inhibitory effect observed with the full-length CaM-KIINtide (here named CN27). The other 21mer peptides, CN21b and CN21c, had minimal or no effect. C-terminal truncations of CN21a by 4 and 7 amino acids significantly impaired inhibition, although CN17a still clearly affected CaMKII activity (FIG. 1B). Thus, the full inhibitory activity is contained in CN21a (CaM-KIIN 43-63). CN21a also blocked phosphorylation of crude liver protein extracts and of bacterially expressed GST-NR2B-c (FIGS. 14A-14C). CN21a (5 µM) blocks CaMKII phosphorylation of (FIG. 14A) crude live protein extracts, (FIG. 14B) bacterially expressed GST-NR2B-c (containing C-terminal NR2B amino acid 1,120 to 1,482), and (FIG. 14C) T305 but not T286 autophosphorylation. Phosphorylation was detected by $^{32}$P autoradiography (FIG. 14A, 14B), or by phosphospecific antibodies (FIG. 14C). In FIGS. 14A and 14B, CaMKII was autophosphorylated before the final reactions 13 min at 30° C.) in order to reduce the T286 signal.

Example 7

Figure 15A:
FIGS. 15A-15D represents affects of various peptides on CaMKII activity. 15A represents, CN19, one minimal inhibitor region of CaM-KIIN. Arrows indicate truncations. 15B-15D represent exemplary histograms of CN19 and further truncations and their inhibitory potency determined by effects on CaMKII activity.
Figure 15B:
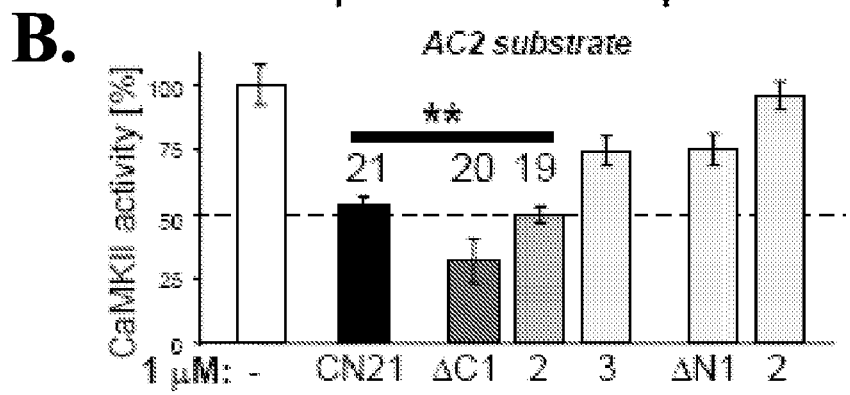
Figure 15C:
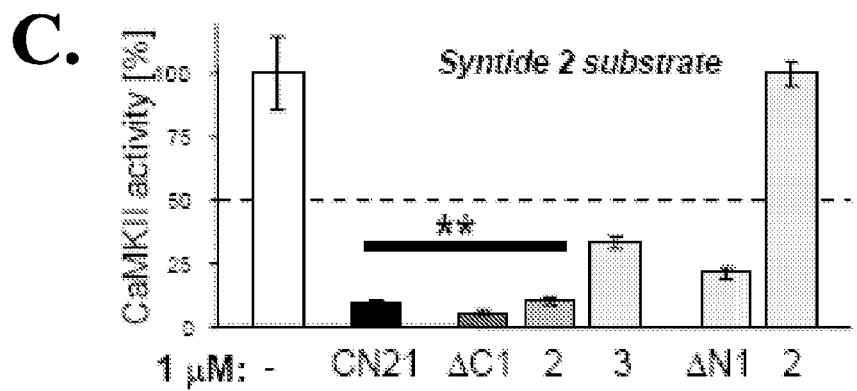
Figure 15D:
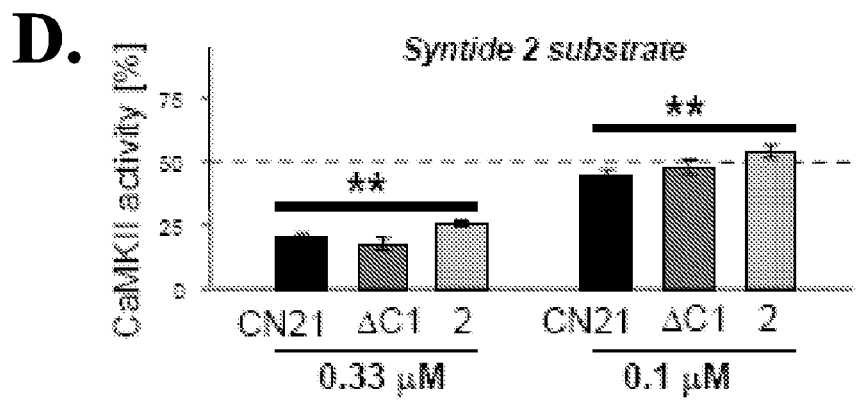

FIGS. 15A-15D represent CN19, a minimal inhibitor region of CaM-KIIN. FIG. 15A represents a previously identified CaM-KIIN inhibitory region, CN21. Arrows indicate truncations that lead to reduced potency of CaMKII inhibition. FIGS. 15B-15D represent that this particular CN19 retains full inhibitory potency, while any other further truncations are shown to reduce inhibitory potency, as determined by the effect on CaMKII activity in a biochemical assay of phosphate incorporation into the substrate peptides AC2 or syntide 2, as indicated. It is contemplated that other reductions or substitution are considered in embodiments herein and that other amino acid sequences of 19 or less amino acids can retain inhibitory capabilities. It is also contemplated that certain amino acid sequences of 21 amino acids or less in this region may be better suited for therapeutic treatments than others. Bars grouped and labeled (**) do not differ from each other as determined by ANOVA. Error bars indicate s.e.m. in all cases.

Figure 16A:
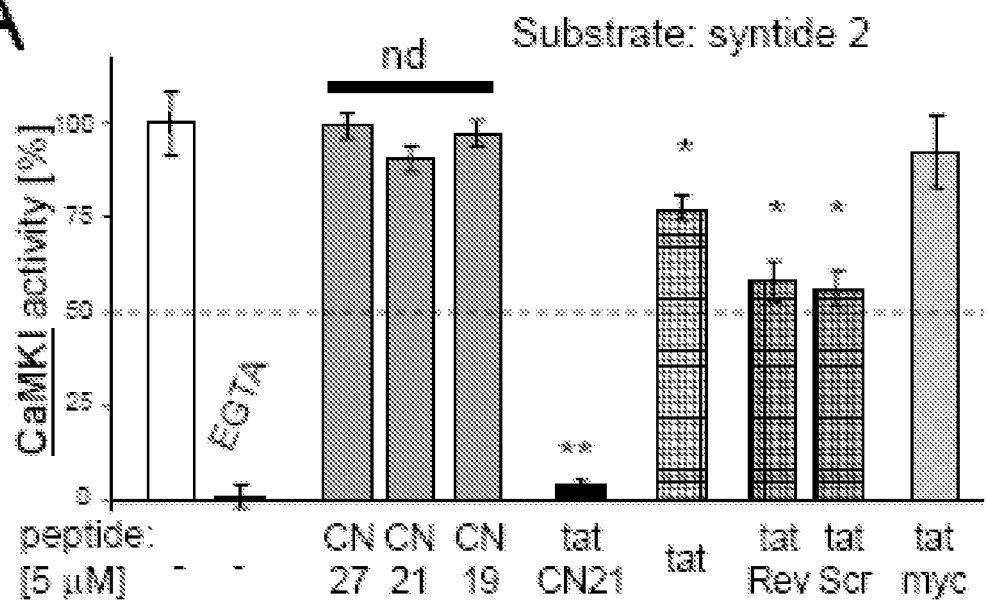
FIGS. 16A and 16B represents various construct effects on CaMKI activity (), tatCN21, as well as, tat alone and other tat fusions, CN27, 21, and 19 alone. 16A represents an exemplary histogram of these effects. 16B** represents an exemplary plot of a dose response of CaMKI inhibition by tatCN21, tat, and CN21.
Figure 16B:
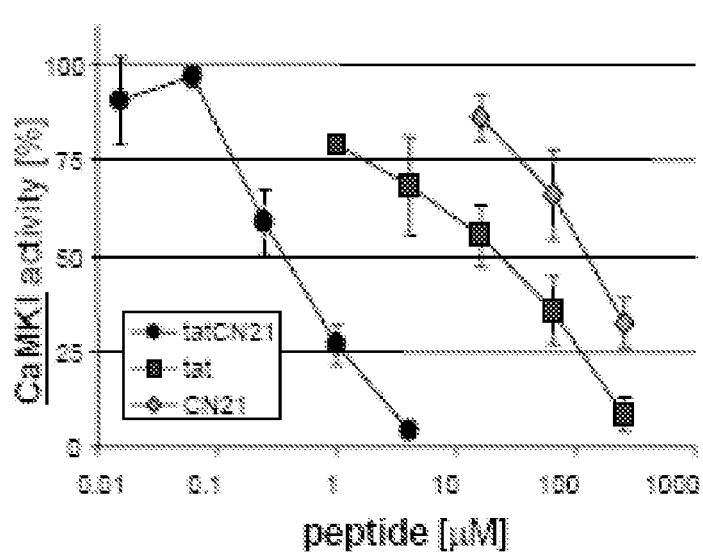

FIGS. 16A and 16B illustrate that tatCN21 dramatically reduces CaMKI activity (**). Tat alone and other tat fusions had statistically significant but much milder effects on CaMKI (*). CN27, 21, and 19 alone had no significant effect on CaMKI activity (nd; ANOVA). FIG. 16B represents a dose response of CaMKI inhibition by tatCN21, tat, and CN21 further demonstrates that CaMKI inhibition dramatically enhanced by the specific fusion. Error bars indicate s.e.m. in all cases.

Example 8

Figures 17A, 17B:
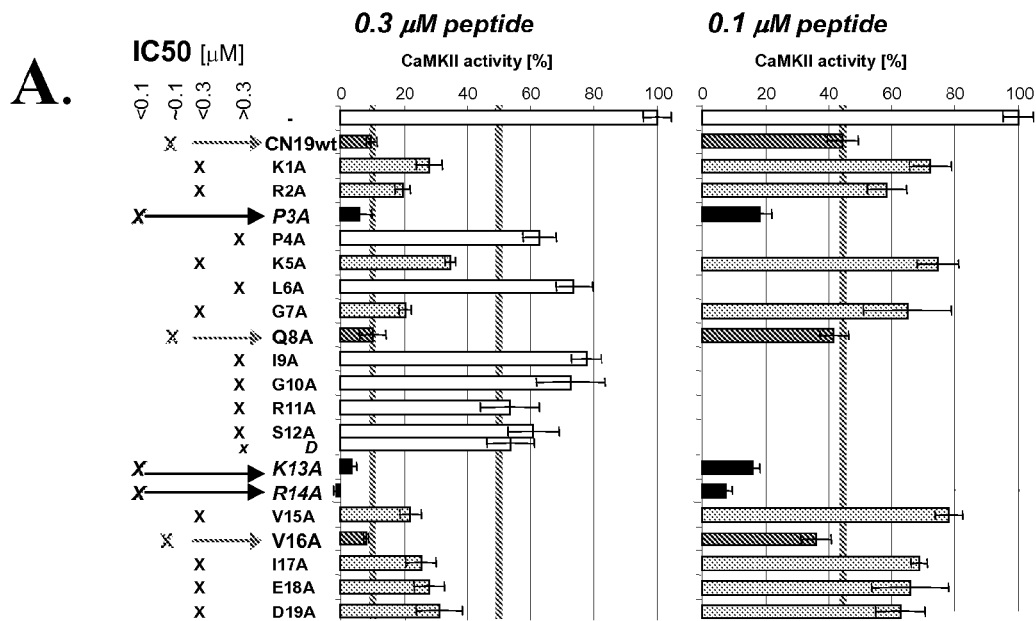
FIGS. 17A-17B represent a summary of the mutational analysis of CN19 and effects on potency of CaMKII inhibition. 17B represents a summary of specific mutations of CN19 on potency of CaMKII inhibition.

In another exemplary method, a mutational analysis of CN19 was performed and effects of CN19 mutations were examined for CaMKII inhibition was analyzed. FIGS. 17A and 17B represent a summary of the mutational analysis of CN19 and effects on potency of CaMKII inhibition. FIG. 17A represents that the first Ala scan of CN19 revealed several mutations that significantly enhanced potency. Error bars indicate s.e.m. FIG. 17B represents a summary of mutational analysis. Three mutations significantly increased potency; two additional ones slightly (the latter ones indicated in non-capital letter). Some specific mutations of S12 are (R, V), while most others are not. Several neutral substitutions for positive residues can be made; the maximal "combination" that remains neutral is the mutant "m1".

In another example, mutations to positively charged amino acids were examined for a portion of the CaMKIIN, CN19. FIG. 18A represents data of several point mutations to Arginine (R) that do not affect potency of CaMKII inhibition identified using a CN19a3 mutant background. FIG. 18B represents the mutant CN19a2-m1 that contains a maximal combination of positively charged mutations without decreasing inhibitory potency. Error bars indicate s.e.m. in all cases. FIG. 18C illustrates additional mutations made in the combination mutatant series, in addition to the 3,14A mutations in CN19a2.

Figure 19A:
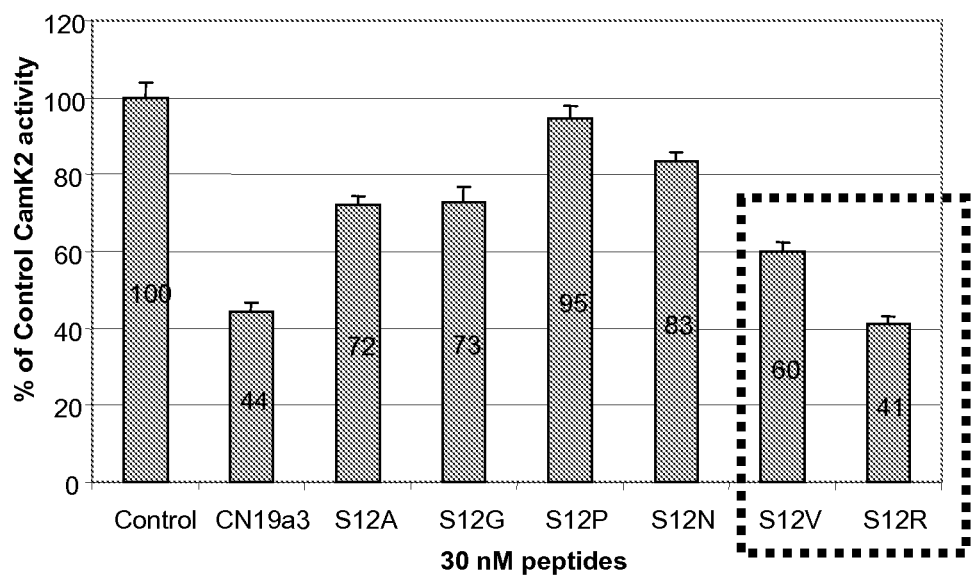
FIGS. 19A-19B represent exemplary histograms of CN19 mutations at S12 and effects of these mutations on CaMKII inhibition. 19A illustrates S12 mutations to potency of CaMKII inhibition. 19B represents an exemplary histogram of the effects S12 mutations in a CN19a2 background on CaMKII activity.
Figure 19B:
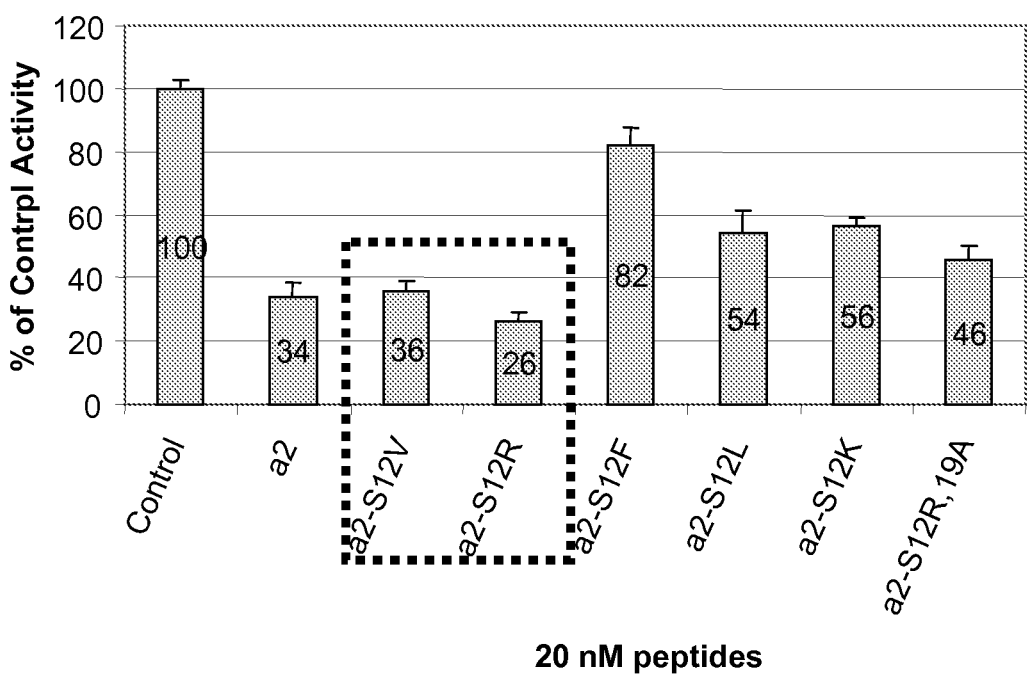

FIGS. 19A and 19B represent CN19 mutations at S12 and effects of these mutations on CaMKII inhibition. FIG. 19A illustrates that most S12 mutations were detrimental to potency of CaMKII inhibition in the context of the CN19a3 mutant (and CN19 wild type; see FIG. 17A, S12 to A and D mutants). However, the S12 to V and R mutants had little effect, or even slightly increased potency of inhibition, respectively. FIG. 19B represents that the same findings were made for the S12 mutations in the CN19a2 background. Thus, S12R (and to some extend S12V) are viable mutations that can prevent phosphorylation of CN peptides within cells, thereby preventing inactivation.

Figure 20A:
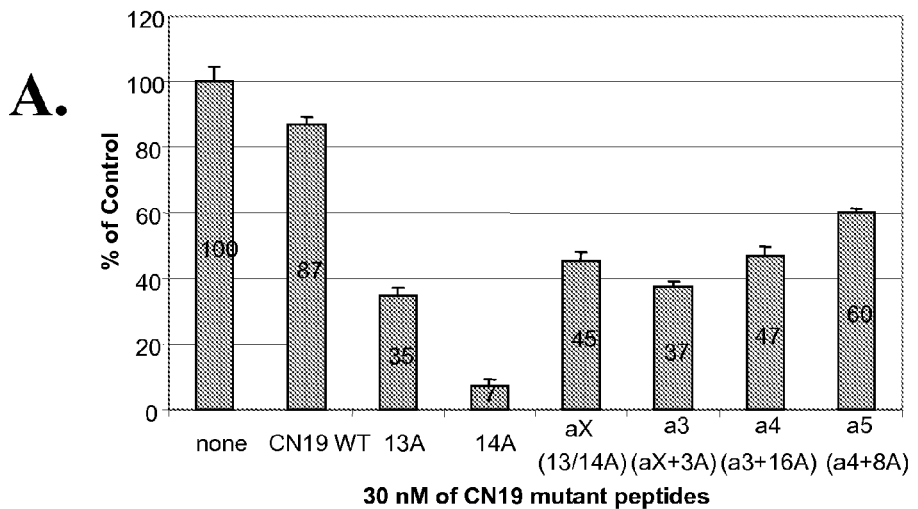
FIGS. 20A-20C represents exemplary histograms of potency of combination mutants of CN19. 20A represents an exemplary histogram of the effects of combination mutants aX, a3, a4, and a5 on potency of CaMKII inhibition compared to CN19 wild type. 20B represents an exemplary histogram of the effects on potency of CaMKII inhibition of other combination mutants at higher concentration. 20C represents an exemplary histogram of the effects on potency of CaMKII inhibition of P4 (see FIG. 17B).
Figure 20B:
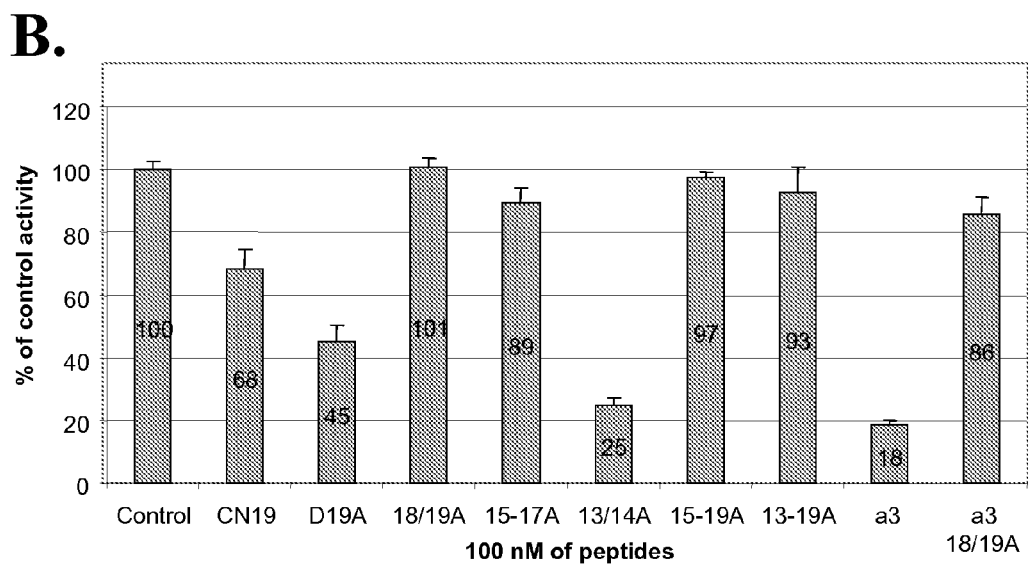
Figure 20C:
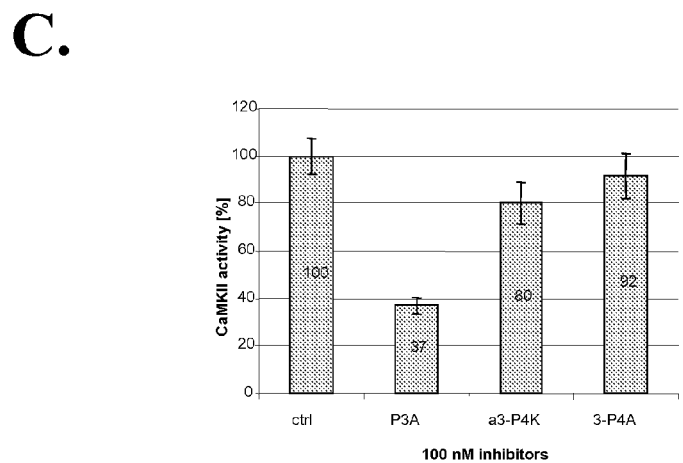

FIGS. 20A-20C illustrate potency of combination mutants I. FIG. 20A represents the combination mutants aX, a3, a4, and a5 that have significantly increased potency of CaMKII inhibition over CN19 wild type. However, potency over the single mutant 13A is mildly increased, if at all, and potency over the single mutant 14A is dramatically decreased. The a3 mutant showed slightly better inhibition than the aX mutant, indicating that a 3,14A mutant (now called a2) might be beneficial over 14A alone. FIG. 20B represents several additional combination mutants at higher concentration. The better inhibition of by a3 compared to aX (13/14A) was confirmed. FIG. 20C represents that P4 appears to be unable to be mutated without reduction in potency, even in a background that contains a P3A mutation. Thus, it is likely that helical structure at the CN19 N-terminus cannot be extended beyond the $3^{rd}$ amino acid. Error bars indicate s.e.m. in all cases.

Figure 21A:
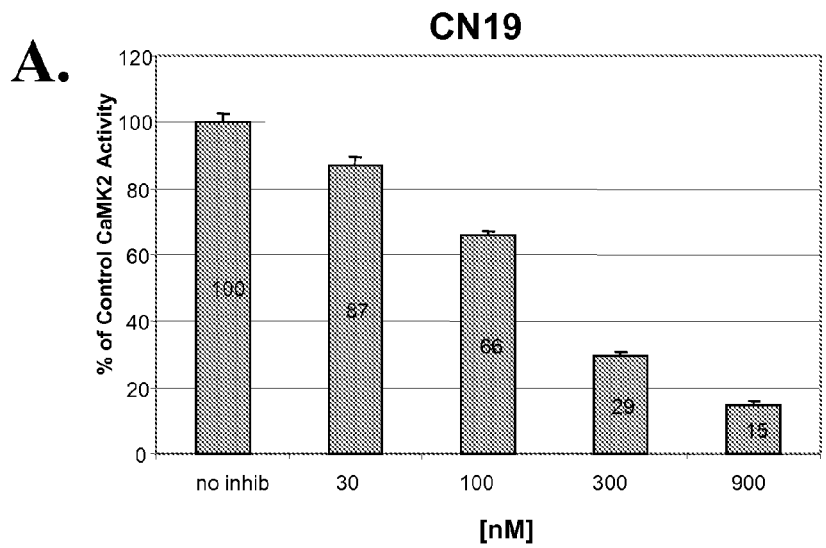
FIGS. 21A-21C represents exemplary histograms of the effects on potency of CaMKII inhibition by combination mutants II. (21A and 21B). 21C represents an exemplary histogram of the effects on potency of CaMKII inhibition by an a2 mutant, an a3 mutant, or an 14A mutant and other mutants as indicated (see FIG. 17B).
Figure 21B:
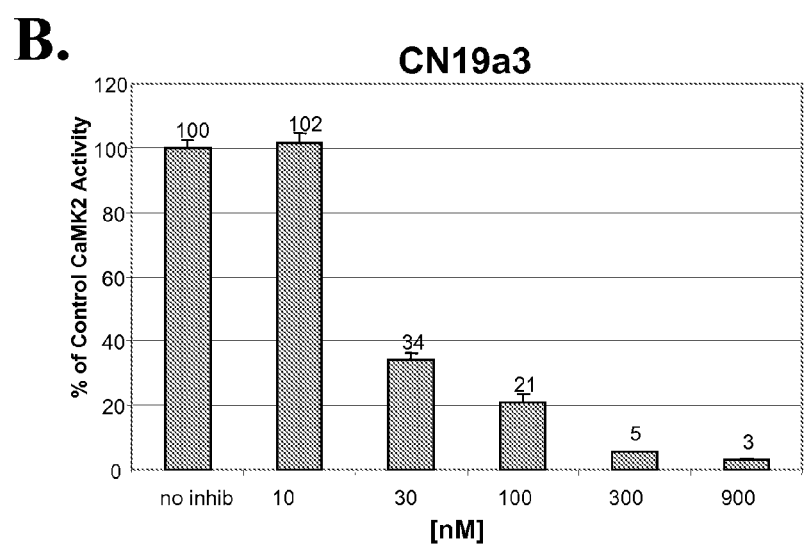
Figure 21C:
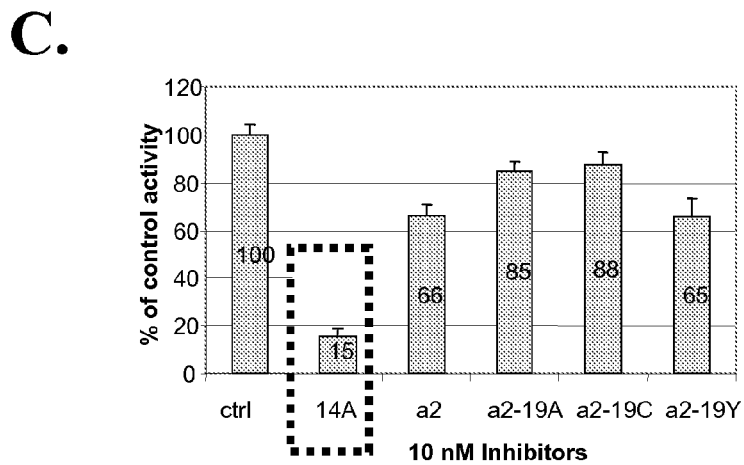

FIGS. 21A-21C represents potency of combination mutants II. (FIGS. 21A and 21B) Dose response showed that potency of the CN19a3 mutant is significantly increased over CN19 wild type. FIG. 21C represents that an a2 mutant has higher potency than the a3 mutant (predicted from FIG. 20), as it shows significant inhibition even at 10 nM (in contrast to a3; see panel B). However, the single mutant 14A has even higher potency, with an IC50 in the single digit nM range. Thus, its potency is increased well over 10 fold compared to CN19 wild type. In context of the a2 mutant, mutations of position 19 to A or C were detrimental, while mutation to Y was not. Error bars indicate s.e.m. in all cases.

Materials and Methods

Peptides and proteins. CaMKIIα and β were purified from a baculovirus/Sf9 cell expression system, CaM was purified after bacterial expression (Bayer et al., 200; incorporated by reference in its entirety). 2-chloro-(ε-amino-Lys$_{75}$)-[6-(4-N, N-diethylaminophenyl)-1,3,5-triazin-4-yl]calmodulin (TA-CaM) was kindly provided (Torok et al., 2000). GFP-CaMKIIα wild type and mutants were expressed in Cos-7 cells and extracts were prepared in 50 mM PIPES, pH 7.2, 10% glycerol, 1 mM EGTA, 1 mM DTT, and protease inhibitors (Boehringer Mannheim). 0.2 g/ml rat liver was homogenized in the same buffer and spun for 10 min at 10,000 g. GST-NR2B-c (amino acids 1,120-1,482 of the cytoplasmic NR2B C-terminus) was expressed in bacteria, previously described. CaM-KIIN, MAP2, AC2, syntide2 (Sigma), calmodulin binding domain (CBD; Calbiochem), tat fusion peptides (Global Peptides), and other CN peptides (Caltech Synthesis Core) were obtained commercially.

CaMKII activity assays. Standard CaMKII assays were done for 1 min at 30° C. previously described, with 20 nM CaMKII (subunit, not holoenzyme concentration), 50 mM PIPES pH 7.2, 0.1 mg/ml BSA, 10 mM $MgCl_2$, 100 µM [γ-$^{32}$P] ATP (~1 Ci/mmol), 1 mM $CaCl_2$, 1-2 µM CaM, and 30-60 µM AC2 peptide (or syntide2). The reactions were spotted onto Whatman P81 phosphocellulose paper rectangles (~2×2.5 cm). To remove free radioactivity, the paper rectangles were rinsed and washed for 30 min under agitation in 0.5% phosphoric acid or water. After two more rinses, an additional 30 min wash typically did not release any more measurable radioactivity. Radioactivity of the bound peptides was quantified in a Beckman 6000TA scintillation counter by the Cherenkov method. Any changes of the standard protocol were done as indicated. For assays of the GFP-CaMKIIα mutants, kinase amounts were normalized by GFP fluorescence in the extract, and total protein was adjusted with Cos-7 extracts.

Kinase panels. A panel of different kinases was tested utilizing a kinase profiling service (Upstate Biotechnology). 40 min reactions at room temperature contained 0.1% BSA and were started by addition of 10 mM MgAcetate and [γ-$^{33}$P-ATP], stopped by 0.1% phosphoryic acid, spotted on filtermats, and washed 3×5 min in 75 mM phosphoric acid and 1× in methanol prior to drying and scintillation counting. CaMKII and IV were activated by 5 mM $CaCl_2$ and 1.7 µM CaM in 40 mM Hepes pH 7.4; substrate was 30 µM KKLN-RTLSVA (SEQ ID NO:22). Buffers and substrates for the other kinases are stated in brackets: PKA (8 mM MOPS pH 7, 0.2 mM EDTA; 30 µM Kemptide), PKCα (20 mM Hepes pH 7.2, 0.3% Triton X-100, 0.1 mg/ml phosphatidylserine, 10 µg/ml diacylglycerol; 0.1 mg/ml histone H1), JNK1α1 (50 mM Tris pH 7.5, 0.1 mM EGTA, 0.1% β-mercapto-ethanol; 3 µM ATF), MAPK1 and raf (25 mM Tris, pH 7.5, 0.02 mM EGTA; 250 µM proprietary substrate and 0.66 mg/ml myelin basic protein, respectively). Reactions in presence of 5 µM CN21a were done in duplicate, and normalized to four parallel reactions without inhibitor.

CaMKII auto- and protein-phosphorylation. 10 nM MAP2 (~140 nM phosphorylation sites) was used instead of substrate peptide, and reaction times were 5 min, unless indicated otherwise. CaMKII concentration was 100 nM subunits (=8.3 nM holoenzymes). Auto- and MAP2-phosphorylation were assessed by Immuno-blot analysis previously derived (Bayer et al., 2002, incorporated herein by reference) with phospho-T286- or -T305-specific antibodies (1:500; PhosphoSolutions) and an anti-phospho-Thr antibody (1:500; Zymed), respectively. Total CaMKIIα was detected with CBα2 antibody (1:2000; GIBCO). Protein were separated on 10% polyacrylamid SDS Gels, and electro-blotted onto "Protran" 0.2 µm pore nitrocelluse filters (e.g. Schleicher & Schull) or onto PVDF filters (e.g. Perkin Elmer). Alternatively, for quantitative analyses, a vacuum-driven slot-blot manifold (e.g. Schleicher & Schull) was used for transfer onto PVDF membranes. PVDF membranes were air-dried for 15 min, then wetted in Methanol. Blots were blocked in 5% milk in TBS-T (Tris-buffered saline pH 7.6 with 0.1% Tween-20). Antibodies were incubated for 45-60 min at room temperature in 2.5% milk in TBS-T; for the anti-phospho-T305 antibody, 2.5% BSA was used instead. After secondary antibody incubation (anti-mouse or anti-rabbit horseradish peroxidase conjugate; Amersham; 1:4000), detection was done using the "Western Lightning" system (Perkin Elmer) and exposure to "Hyperfilm" (Amersham). For quantitative analysis, chemoluminescence was captured using a ChemiImager 4400 imaging system (Alpha Innotek) instead of film. Only non-saturated images were analyzed, using AlphaEase software.

Crude liver extracts or NR2B-c were phosphorylated with 100 nM autophosphorylated CaMKII, 2 µM CaM and 40 µM [γ-$^{32}$P]-ATP (~2 Ci/mmole). Pre-auto-phosphorylation (of 300 nM CaMKII) was done for 5 min on ice, in presence of 3 mM $CaCl_2$, 6 µM CaM and 120 µM unlabelled ATP. After addition of [γ-$^{32}$P]-ATP and inhibitors as indicated, 2 min reactions at 30° C. were started by addition of substrate protein extract ($1/3^{rd}$ to $1/12^{th}$ of total reaction volume), and stopped with 25 mM EDTA. Phosphorylation was detected by autoradiography after gel electrophoresis.

CaMKII binding to NR2B-c was assessed as previously described. Briefly, GST-NR2B-c was immobilized on anti-GST coated microtiter plates, then overlaid with 100 nM CaMKII in presence of $Ca^{2+}$/CaM and 1 or 5 µM of various CN peptides. After extensive wash, protein was eluted from the plates by boiling in SDS-loading buffer. Eluted CaMKII was detected by Western-blot as described above.

TA-CaM dissociation was assessed by increased TA-CaM (30 nM) fluorescence after dissociation from CaMKII or its CaM-binding domain (CBD) (150 nM) during a chase with unlabeled CaM (60 µM). Buffer contained 50 mM Hepes pH 7.4, 150 mM KCl, 2 mM $MgCl_2$, 2 mM MgADP, 2 mM $CaCl_2$, and 0.1 mg/ml BSA. Fluorescence was measured in a time scan (1 sec samples) at 365 nm excitation and 415 nm emission wavelength on a spectro-fluorometer (Fluorolog3; Horiba Jobin Yvon) and was corrected for photobleach (FIG. 16).

Imaging of neuronal filopodia motility was done similarly as previously described. Hippocampal cultures were prepared from newborn Sprague Dawley rats (Harlan) as previously described, plated onto poly-D-lysine coated glass bottom dishes (MatTek) at a density of ~2.5×10$^6$ cells/cm$^2$ and maintained in Neurobasal A medium with penicillin/streptomycin (50 units/ml), glutamax (2 mM) and B27 supplement (Invitrogen). Glial growth was inhibited by 5-fluoro-2'-deoxy-uridine and uridine (70 µM and 140 µM). After 5 days in vitro, neurons were transfected with a GFP expression construct (Clonetech) using lipofectamine 2000 (Invitrogen), as described. On the next day neurons were imaged in culture medium on for example, a Zeiss Axiovert 200M systems equipped with a 40× oil immersion objective, Cool Snap HQ CCD camera (Roeper Scientific), Xenon lamp LB-LS/17 (Sutter Instruments) and climate control set to 30° C. and 5% $CO_2$. Fluorescence Images were acquired and analyzed using SlideBook software (Intelligent Imaging Innovations). 16 images were taken in 20 s time intervals, at 100 ms exposure time and bin factor 2. Subtraction image (Δ image) stacks were generated by subtracting one stack (first image deleted) from its duplicate (last image deleted). Then, Δ image stacks were converted into average images in pseudocolor, for better visualization of motility. Quantification of the pixel intensity yielded a relative motility index, expressed as Δ image intensity before treatment set as 100%. Intensity cutoff masks eliminated most background pixels not located within neurons. Neurons were imaged before and after 20 min incubation with either tatCN21 or tatRev (5 µM). Incubation was done on the imaging setup; data from experimental days on which mock incubation without peptide affected motility were discarded.

Insulin secretion. Langerhans' islets acutely isolated from adult male Wistar rats (Harlan) were obtained. On 24-well plates, 10 islets were pooled per well in 20 mM Hepes, 25 mM $NaHCO_3$, 114 mM NaCl, 4.7 mM KCl, 1.2 mM $KH_2PO_4$, 1.16 mM $MgSO_4$, 2.5 mM $CaCl_2$, 0.2% BSA; adjusted to pH 7.2. Within 90 min after isolation, insulin secretion was stimulated with 11 mM glucose. Inhibitors or EGTA were added 30 min before stimulation. Insulin secreted into the medium during 90 min stimulation was measured using an ELISA kit (CrystalChem). Two independent islet preparations showed inhibition of glucose-stimulated insulin secretion by tatCN21.

All of the COMPOSITIONS and/or METHODS disclosed and claimed herein can be made and executed without undue experimentation in light of the present disclosure. While the compositions and methods of this invention have been described in terms of preferred embodiments, it will be apparent to those of skill in the art that variation may be applied to the COMPOSITIONS and/or METHODS described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

What is claimed is:

1. A composition comprising a peptide consisting of 19, 20 or 21 consecutive amino acids of the sequence of SEQ ID NO:1 or a pharmaceutically acceptable derivative or salt thereof.

2. The composition of claim 1, further comprising a cell-transfer/penetrating agent associated with the peptide.

3. The composition of claim 2, wherein the cell-transfer/penetrating agent is fused to the peptide.

4. The composition of claim 2, wherein the cell-transfer/penetrating agent comprises tat, ant, meristyl-group, palmityl-group or combination thereof.

5. The composition of claim 1, wherein the peptide is 19 consecutive amino acids of SEQ ID NO:1.

6. The composition of claim 2, further comprising one or more agents for treating a neurodegenerative condition.

7. A composition comprising a peptide consisting of 19, 20 or 21 consecutive amino acids of the sequence Lys Arg Xaa1 Pro Lys Leu Gly Gln Ile Gly Arg Xaa2 Xaa3 Arg Val Val Ile Glu Asp Asp Arg (SEQ ID NO. 23), wherein position 3, Xaa1, is selected from the group consisting of proline, alanine, arginine or lysine; position 12, Xaa2, is selected from the group consisting of serine, valine or arginine; and position 13, Xaa3, is selected from the group consisting of lysine or alanine, or a pharmaceutically acceptable derivative or salt thereof.

8. A kit comprising:
a vessel; and
one or more compositions comprising one or more of the compositions of claim 1 or claim 7.

9. The kit of claim 8, further comprising a delivery device for administering the one or more compositions.

* * * * *

SEQUENCE LISTING

```
<160> NUMBER OF SEQ ID NOS: 23

<210> SEQ ID NO 1
<211> LENGTH: 21
<212> TYPE: PRT
<213> ORGANISM: Artificial Sequence
<220> FEATURE:
<223> OTHER INFORMATION: derived from CaM-KIIN

<400> SEQUENCE: 1

Lys Arg Pro Pro Lys Leu Gly Gln Ile Gly Arg Ser Lys Arg Val Val
1               5                   10                  15

Ile Glu Asp Asp Arg
            20

<210> SEQ ID NO 2
<211> LENGTH: 19
<212> TYPE: PRT
<213> ORGANISM: Artificial Sequence
<220> FEATURE:
<223> OTHER INFORMATION: derived from CaM-KIIN

<400> SEQUENCE: 2

Lys Arg Pro Pro Lys Leu Gly Gln Ile Gly Arg Ser Lys Arg Val Val
1               5                   10                  15

Ile Glu Asp

<210> SEQ ID NO 3
<211> LENGTH: 19
<212> TYPE: PRT
<213> ORGANISM: Artificial Sequence
<220> FEATURE:
<223> OTHER INFORMATION: derived from CaM-KIIN with a point mutation

<400> SEQUENCE: 3

Lys Arg Ala Pro Lys Leu Gly Gln Ile Gly Arg Ser Lys Arg Val Val
1               5                   10                  15

Ile Glu Asp

<210> SEQ ID NO 4
<211> LENGTH: 19
<212> TYPE: PRT
<213> ORGANISM: Artificial Sequence
<220> FEATURE:
<223> OTHER INFORMATION: derived from CaM-KIIN with point mutation

<400> SEQUENCE: 4

Lys Arg Pro Pro Lys Leu Gly Gln Ile Gly Arg Arg Lys Arg Val Val
1               5                   10                  15

Ile Glu Asp

<210> SEQ ID NO 5
<211> LENGTH: 19
<212> TYPE: PRT
```

-continued

```
<213> ORGANISM: Artificial Sequence
<220> FEATURE:
<223> OTHER INFORMATION: derived from CaM-KIIN with point mutation

<400> SEQUENCE: 5

Lys Arg Pro Pro Lys Leu Gly Gln Ile Gly Arg Val Lys Arg Val Val
1               5                   10                  15

Ile Glu Asp

<210> SEQ ID NO 6
<211> LENGTH: 19
<212> TYPE: PRT
<213> ORGANISM: Artificial Sequence
<220> FEATURE:
<223> OTHER INFORMATION: derived from CaM-KIIN with point mutation

<400> SEQUENCE: 6

Lys Arg Pro Pro Lys Leu Gly Gln Ile Gly Arg Ser Ala Arg Val Val
1               5                   10                  15

Ile Glu Asp

<210> SEQ ID NO 7
<211> LENGTH: 19
<212> TYPE: PRT
<213> ORGANISM: Artificial Sequence
<220> FEATURE:
<223> OTHER INFORMATION: derived from CaM-KIIN with point mutation

<400> SEQUENCE: 7

Lys Arg Pro Pro Lys Leu Gly Gln Ile Gly Arg Ser Lys Ala Val Val
1               5                   10                  15

Ile Glu Asp

<210> SEQ ID NO 8
<211> LENGTH: 19
<212> TYPE: PRT
<213> ORGANISM: Artificial Sequence
<220> FEATURE:
<223> OTHER INFORMATION: derived from CaM-KIIN with point mutations

<400> SEQUENCE: 8

Lys Arg Ala Pro Lys Leu Gly Gln Ile Gly Arg Ser Lys Ala Val Val
1               5                   10                  15

Ile Glu Asp

<210> SEQ ID NO 9
<211> LENGTH: 19
<212> TYPE: PRT
<213> ORGANISM: Artificial Sequence
<220> FEATURE:
<223> OTHER INFORMATION: derived from CaM-KIIN with point mutations

<400> SEQUENCE: 9

Lys Arg Pro Pro Lys Leu Gly Gln Ile Gly Arg Arg Lys Ala Val Val
1               5                   10                  15

Ile Glu Asp

<210> SEQ ID NO 10
<211> LENGTH: 19
<212> TYPE: PRT
<213> ORGANISM: Artificial Sequence
<220> FEATURE:
<223> OTHER INFORMATION: derived from CaM-KIIN with point mutations
```

-continued

```
<400> SEQUENCE: 10

Lys Arg Ala Pro Lys Leu Gly Gln Ile Gly Arg Arg Lys Ala Val Val
1               5                   10                  15

Ile Glu Asp

<210> SEQ ID NO 11
<211> LENGTH: 19
<212> TYPE: PRT
<213> ORGANISM: Artificial Sequence
<220> FEATURE:
<223> OTHER INFORMATION: derived from CaM-KIIN with point mutations

<400> SEQUENCE: 11

Lys Arg Pro Pro Lys Leu Gly Gln Ile Gly Arg Val Lys Ala Val Val
1               5                   10                  15

Ile Glu Asp

<210> SEQ ID NO 12
<211> LENGTH: 19
<212> TYPE: PRT
<213> ORGANISM: Artificial Sequence
<220> FEATURE:
<223> OTHER INFORMATION: derived from CaM-KIIN with point mutations

<400> SEQUENCE: 12

Lys Arg Ala Pro Lys Leu Gly Gln Ile Gly Arg Val Lys Ala Val Val
1               5                   10                  15

Ile Glu Asp

<210> SEQ ID NO 13
<211> LENGTH: 19
<212> TYPE: PRT
<213> ORGANISM: Artificial Sequence
<220> FEATURE:
<223> OTHER INFORMATION: derived from CaM-KIIN with amino acid
      substitutions

<400> SEQUENCE: 13

Lys Arg Arg Pro Arg Leu Arg Gln Ile Gly Arg Arg Lys Ala Val Val
1               5                   10                  15

Ile Glu Asp

<210> SEQ ID NO 14
<211> LENGTH: 32
<212> TYPE: PRT
<213> ORGANISM: Artificial Sequence
<220> FEATURE:
<223> OTHER INFORMATION: derived from CaM-KIIN with a cell penetrating
      sequence

<400> SEQUENCE: 14

Tyr Gly Arg Lys Lys Arg Arg Gln Arg Arg Lys Arg Pro Pro Lys
1               5                   10                  15

Leu Gly Gln Ile Gly Arg Ser Lys Arg Val Val Ile Glu Asp Asp Arg
                20                  25                  30

<210> SEQ ID NO 15
<211> LENGTH: 11
<212> TYPE: PRT
<213> ORGANISM: Artificial Sequence
<220> FEATURE:
<223> OTHER INFORMATION: cell penetrating sequences

<400> SEQUENCE: 15
```

```
Tyr Gly Arg Lys Lys Arg Arg Gln Arg Arg Arg
1               5                   10

<210> SEQ ID NO 16
<211> LENGTH: 15
<212> TYPE: PRT
<213> ORGANISM: Artificial Sequence
<220> FEATURE:
<223> OTHER INFORMATION: cell penetrating sequences

<400> SEQUENCE: 16

Arg Gln Ile Lys Ile Trp Phe Gln Asn Arg Arg Met Lys Trp Lys
1               5                   10                  15

<210> SEQ ID NO 17
<211> LENGTH: 27
<212> TYPE: PRT
<213> ORGANISM: Artificial Sequence
<220> FEATURE:
<223> OTHER INFORMATION: derived from CaM-KIIN sequence

<400> SEQUENCE: 17

Lys Arg Pro Pro Lys Leu Gly Gln Ile Gly Arg Ser Lys Arg Val Val
1               5                   10                  15

Ile Glu Asp Asp Arg Ile Asp Asp Val Leu Lys
            20                  25

<210> SEQ ID NO 18
<211> LENGTH: 21
<212> TYPE: PRT
<213> ORGANISM: Artificial Sequence
<220> FEATURE:
<223> OTHER INFORMATION: derived from CaM-KIIN sequence

<400> SEQUENCE: 18

Pro Lys Leu Gly Gln Ile Gly Arg Ser Lys Arg Val Val Ile Glu Asp
1               5                   10                  15

Asp Arg Ile Asp Asp
            20

<210> SEQ ID NO 19
<211> LENGTH: 21
<212> TYPE: PRT
<213> ORGANISM: Artificial Sequence
<220> FEATURE:
<223> OTHER INFORMATION: derived from CaM-KIIN sequence

<400> SEQUENCE: 19

Gly Gln Ile Gly Arg Ser Lys Arg Val Val Ile Glu Asp Asp Arg Ile
1               5                   10                  15

Asp Asp Val Leu Lys
            20

<210> SEQ ID NO 20
<211> LENGTH: 17
<212> TYPE: PRT
<213> ORGANISM: Artificial Sequence
<220> FEATURE:
<223> OTHER INFORMATION: derived from CaM-KIIN sequence

<400> SEQUENCE: 20

Lys Arg Pro Pro Lys Leu Gly Gln Ile Gly Arg Ser Lys Arg Val Val
1               5                   10                  15

Ile
```

```
<210> SEQ ID NO 21
<211> LENGTH: 14
<212> TYPE: PRT
<213> ORGANISM: Artificial Sequence
<220> FEATURE:
<223> OTHER INFORMATION: derived from CaM-KIIN sequence

<400> SEQUENCE: 21

Lys Arg Pro Pro Lys Leu Gly Gln Ile Gly Arg Ser Lys Arg
1               5                   10

<210> SEQ ID NO 22
<211> LENGTH: 10
<212> TYPE: PRT
<213> ORGANISM: Artificial Sequence
<220> FEATURE:
<223> OTHER INFORMATION: substrate

<400> SEQUENCE: 22

Lys Lys Leu Asn Arg Thr Leu Ser Val Ala
1               5                   10

<210> SEQ ID NO 23
<211> LENGTH: 21
<212> TYPE: PRT
<213> ORGANISM: Artificial Sequence
<220> FEATURE:
<223> OTHER INFORMATION: derived from CaM-KIIN
<220> FEATURE:
<221> NAME/KEY: MISC_FEATURE
<222> LOCATION: (3)..(3)
<223> OTHER INFORMATION: Xaa is Pro, Ala, Arg or Lys
<220> FEATURE:
<221> NAME/KEY: MISC_FEATURE
<222> LOCATION: (12)..(12)
<223> OTHER INFORMATION: Xaa is Ser, Val, or Arg
<220> FEATURE:
<221> NAME/KEY: MISC_FEATURE
<222> LOCATION: (13)..(13)
<223> OTHER INFORMATION: Xaa is Lys, or Ala

<400> SEQUENCE: 23

Lys Arg Xaa Pro Lys Leu Gly Gln Ile Gly Arg Xaa Xaa Arg Val Val
1               5                   10                  15

Ile Glu Asp Asp Arg
                20
```